(12) United States Patent
Sun

(10) Patent No.: US 8,449,824 B2
(45) Date of Patent: May 28, 2013

(54) SENSOR INSTRUMENT SYSTEM INCLUDING METHOD FOR DETECTING ANALYTES IN FLUIDS

(76) Inventor: Yizhong Sun, Castaic, CA (US)

( * ) Notice: Subject to any disclaimer, the term of this patent is extended or adjusted under 35 U.S.C. 154(b) by 1129 days.

(21) Appl. No.: 12/217,261

(22) Filed: Jul. 2, 2008

(65) Prior Publication Data

US 2009/0261987 A1     Oct. 22, 2009

Related U.S. Application Data

(63) Continuation-in-part of application No. 10/238,794, filed on Sep. 9, 2002, now Pat. No. 7,465,425.

(51) Int. Cl.
  *G01N 27/00* (2006.01)
  *G01N 27/327* (2006.01)
  *G01N 33/543* (2006.01)
  *G01N 27/414* (2006.01)
  *B82Y 15/00* (2006.01)

(52) U.S. Cl.
  CPC ........ *G01N 27/3271* (2013.01); *G01N 33/5438* (2013.01); *G01N 27/414* (2013.01); *G01N 33/54373* (2013.01); *B82Y 15/00* (2013.01)
  USPC ......... 422/82.01; 422/52; 422/73; 422/82.05; 422/82.08; 422/82.09; 422/82.11; 422/407; 422/501; 422/502; 422/503; 422/504; 436/149; 436/150; 436/151; 436/164; 436/177; 436/43; 436/63; 435/29; 435/4; 435/7.1; 506/30; 250/214.1; 250/251; 250/576; 530/408; 714/752

(58) Field of Classification Search
  CPC ............ G01N 27/3271; G01N 33/5438; G01N 27/414; G01N 33/54373; B82Y 15/00
  USPC .......... 422/63, 68.1, 76, 82.01, 82.02, 82.03, 422/82.04, 88, 90, 98, 52, 73, 82.05, 82.08, 422/82.09, 82.11, 99, 102, 407, 501, 502, 422/503, 504; 436/149, 150, 151, 164, 177, 436/43, 63; 435/29, 4, 6, 7.1; 506/30; 250/214.1, 251, 576; 530/408; 714/752
  See application file for complete search history.

(56) References Cited

U.S. PATENT DOCUMENTS

| | | | |
|---|---|---|---|
| 5,788,833 A * | 8/1998 | Lewis et al. | 205/787 |
| 5,882,497 A * | 3/1999 | Persaud et al. | 205/188 |
| 2004/0204915 A1* | 10/2004 | Steinthal et al. | 702/188 |
| 2006/0105467 A1* | 5/2006 | Niksa et al. | 436/150 |

* cited by examiner

*Primary Examiner* — Dennis M White
(74) *Attorney, Agent, or Firm* — Thomas I. Rozsa

(57) ABSTRACT

A sensor instrument system for detecting and identifying analytes in fluids of a region contains a local sensor instrument and remote central station. The instrument includes a core technology employing a single sensor having two electrodes operated by an electrical frequency sweeping to generate two sets of patterned electrical information from a single measurement, a data transmission module and a GPS receiver module. The central station connects to a network means connected to a plurality of local receiving sites equipped with including the respective transceivers, so that the local analyte electrical information and geographic position information transmitted by the instrument can be wirelessly and remotely received and processed by the central station. The core technology further includes a reference sensor for eliminating background influence, a temperature programming to control adsorption and desorption of analytes, and usage of all kinds of adsorbent materials having chemical selectivities including the hydrogen selectivity to enhance detection and identification of analytes in fluids.

33 Claims, 7 Drawing Sheets

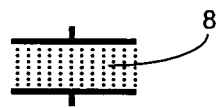 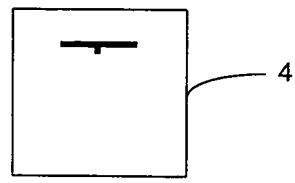
FIG. 6  FIG. 7A
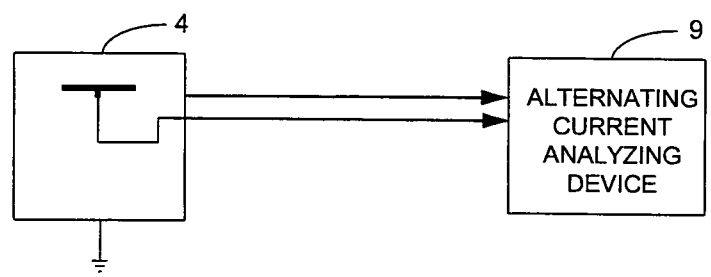
FIG. 7B
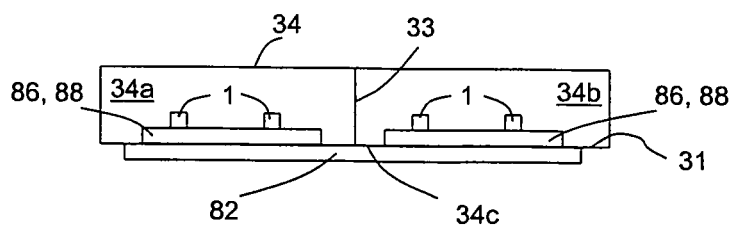
FIG. 10

SENSOR INSTRUMENT SYSTEM INCLUDING METHOD FOR DETECTING ANALYTES IN FLUIDS

This application is a continuation-in-part of application Ser. No. 10/238,794 filed on Sep. 9, 2002, which is now U.S. Pat. No. 7,465,425.

BACKGROUND OF THE INVENTION

1. Field of the Invention

The present invention relates generally to the field of sensor instruments, and more particularly relates to a sensor instrument system including methods for detecting analytes in fluids.

2. Description of the Prior Art

Sensor instruments are widely used in the technology of detecting analytes present in fluids. The following references are pertinent to this field of art:

1. U.S. Pat. No. 4,887,455 issued on Dec. 19, 1989 to Payne et al. for "Gas Sensor" (hereafter "the '455 Payne Patent");
2. U.S. Pat. No. 5,571,401 issued on Nov. 5, 1996 to Lewis et al. for "Sensor Arrays for Detecting Analytes in Fluids" (hereafter "the '401 Lewis Patent");
3. U.S. Pat. No. 6,319,724 issued on Nov. 20, 2001 to Lewis et al. for "Trace Level Detection of Analytes Using Artificial Olfactometry" (hereafter "the '724 Lewis Patent");
4. Payne, et al., "High-Frequency Measurements of Conducting Polymers: Development of A New Technique for Sensing Volatile Chemicals", Meas. Sci. Technol. 6 (1995) pp. 1500-1507 (hereafter "the Payne Publication");
5. Nagle, H. T., et al., "The How And Why Of Electronic Nose", IEEE Spectrum, September 1998, pp. 22-34 (hereafter "the Nagle Publication");
6. Baltes, H., et al., "The Electronic Nose In Lilliput", IEEE Spectrum, September 1998, pp. 35-38 (hereafter "the Baltes Publication"); and
7. U.S. Pat. No. 6,631,333 issued on Oct. 7, 2003 to Lewis et al. for "Methods For Remote Characterization Of An Odor" (hereafter "the '333 Lewis Patent", in addition to U.S. Pat. No. 7,359,802 issued on Apr. 15, 2008 to the same inventors, which is a Divisional Patent of the '333 Lewis Patent); and
8. U.S. Pat. No. 7,465,425 issued on Dec. 16, 2008 to Sun for "Sensor And Method For Detecting Analytes In Fluids" (hereafter "the '425 Sun Patent").

The '455 Payne Patent discloses a gas sensor that has a semiconductor organic polymer layer exposed to a gas to be detected. An analyzer applies an alternating electric signal at specific resonant frequencies to the sensor to detect the change in the sensor's impedance characteristics which is compared by a microcomputer with reference characteristics stored in a memory of the microcomputer. The gas in contact with the sensor can be detected because of the resulting difference spectra. The patent further discloses that the best performance of the invention is likely to be conducted between frequencies ranging 100 MHZ to 500 MHZ where the resonance may happen.

The '401 Lewis Patent discloses arrays of chemical sensors, including polymer carbon powder based chemiresistor for detecting analytes in fluids. The sensors include first and second conductive elements electrically coupled to and separated by a chemically sensitive resistor which provides an electrical path between the conductive elements. The resistor includes a plurality of alternating nonconductive regions made of a nonconductive organic polymer and conductive regions made of a conductive material transverse to the electrical path. The resistor further provides a difference in resistance between the conductive elements when contacted with a fluid containing a chemical analyte at a first concentration, and then at a second different concentration. Arrays of such sensors are constructed with at least two sensors having different chemically sensitive resistors providing differences in resistance. Variability in chemical sensitivity from sensor to sensor is provided by qualitatively or quantitatively varying the composition of the conductive and/or nonconductive regions. An "electronic nose" for detecting an analyte in a fluid may be constructed by using such arrays in conjunction with an electrical measuring device electrically connected to the conductive elements of each sensor.

The '724 Lewis Patent discloses a method using artificial olfactometry for detecting the presence of an analyte indicative of various medical conditions, including halitosis, periodontal disease and other diseases.

The Payne Publication discloses the change in the alternating current (AC) impedance characteristics of poly-N-(2-pyridyl) pyrrole in the presence of different volatile chemicals.

The Nagle Publication is a special report, which summarizes research and development of the electronic nose instrument through 1990's. The report introduces in detail types of sensors including the respective sensing mechanisms for metal oxide thin film resistor sensors, conductive polymer sensors, polymer coated quartz crystal microbalance (QCM) sensors, polymer coated surface acoustic wave (SAW) sensors, metal-oxide-silicon field-effect-transistor (MOSFET) sensors, dye coated optical fiber (DCOF) sensors, gas chromatography (GC), light spectrum, and mass spectrometry (MS). The report also discloses advantages and disadvantages according to the respective sensors including the sensing mechanisms, wherein a high sensitivity to humidity is addressed as the disadvantage of the polymer film based sensors.

The Baltes Publication reports the developed micronose integrated circuit sensor CMOS chip coated with polymer films according to mechanisms of sensing mass change and dielectric constant change of the polymer films when they load up on volatile organic compounds.

The '333 Lewis Patent discloses compositions and systems useful in remote monitoring of chemical hazards, air quality and medical conditions. For example, robotic systems search for and detect explosives, mines, and hazardous chemicals. In addition, the methods, systems and compositions of the invention provide the ability to mine data from database containing a plurality of chemical fingerprints. The Patent also summarizes techniques for constructing sensors as disclosed in the Nagle Publication, in addition to a dye-impregnated bread (DIB) arrays and micromachined cantilver (MMC) arrays. The Patent further discloses the invented electrically conductive sensor that comprises alternating regions of a conductive material and a material compositionally different than the conductive material between two conductive leads wherein said sensor provides an electrical path through the regions of conductive material and the regions of the compositionally different material.

It can be seen from the above cited references that significant efforts have been devoted in the past in the research and development of sensor instrument systems, which is centered on the studying of sensors. This is because configuration of the sensors predominantly governs sensor instrument performance for detecting and identifying analytes in fluids. In instrument analysis, identification of analytes in fluids is accomplished through applying sensors which mimic mechanisms of the mammalian olfactory system that applies probabilistic repertoires of many different receptors to record a single odorant. Having such sensor technologies in conjunction with existing technologies in electrical engineering including highly integrated circuit chips (ICs), advanced softwares, remote data transmission, the current sensor instrument improves convenience in the analyte detection and identification.

It is well known that, from studying the mammalian olfactory system, identification of the odorant is dependent upon not only the results from highly specific receptors but also the output from less specific ones. In other words, identification is based on recognition a of a spectrum of signals that resemble a specific pattern. Following this direction, conventional technologies in sensor configuration are developed according to the following two schemes to generate a signal spectrum: applying strategies of a multiple sensor configuration and a single sensor configuration.

In the approaches that utilize the multiple sensor strategy, which are disclosed by the Nagle Publication in addition to the '333 Lewis Patent, various detecting devices have been developed that use metal oxide thin film resistor sensors, conductive polymer or polymer carbon powder composite film chemi-resistor sensors, QCM, SAW, MOSFET and DCOF sensors, and DIB and MMC arrays. However, although much progress has been made in the past, there are still primary disadvantages inherited from the sensing mechanisms of such multiple sensor technologies. The disadvantages include the requirement of a large number of sensors to generate a patterned information, the sophistication of the sensor configuration, thus the resulting poor reproducibility in sensor manufacturing, the strong humidity influence applying polymer film modified sensors on chemical analysis, the slow response, the expensive electronic equipment required, and the very restricted operating conditions.

Various polymer films with a general thickness of several micrometers have been extensively used in the multiple sensor strategy to improve sensor sensitivity and detection limit. This is primarily due to the fact that the polymer films can trap including adsorbing and absorbing analytes of chemicals, according to their specific chemical selectivities on the analytes. As a result, the analytes will be concentrated on the surfaces or inside of the polymer films prior to detection.

However, the conventional polymer films also inherit a number of disadvantages. First, the thin films of polymer are sensitive to the humidity associated with analytes. Humidity is the predominant factor to influence performance of the polymer film based gas sensors. Second, polymer films have an aging effect that affects the sensor stability for long term usages. Third, it is difficult to achieve reproducibility of the polymer films positioned in sensors, particularly in a situation when a large number of the sensors must be used according to the multiple sensor strategy.

In the approaches that utilize a single sensor strategy also disclosed by the Nagle Publication, various instruments have been developed that are based on the mechanisms of GC, MS, and light spectrum. Generally, these instruments are very expensive. Moreover, they are typically very bulky in size, which makes their miniaturization almost impossible. As a result, they are less attractive in the market, where portability of the instruments having wireless communication capabilities becomes increasingly important.

For example, a strategy of point-of-care (POC) is becoming an urgent demand in the field of medical diagnoses. Under the strategy POC, patient healthcare including medical diagnoses are directly conducted at the patients' bedsides of the respective patients' homes. Therefore, medical instruments are advantageous if they are completely portable. In addition, it is significantly advantageous if the instruments can have wireless and remote data communication capabilities, so that patients' health information can be in situ transmitted to a medical center for better patient treatment. In fact, instruments having portabilities and wireless communication capabilities are critical in many fields besides the medical field, including security, military and industrial fields.

As an example utilizing the single sensor strategy, the Payne Patent and Payne Publication discussed above disclose application of a single sensor for detecting the presence of gaseous analytes from detecting impedance and phase sensitive components of conductive polymer modified electrodes at specific frequencies, where electrical resonant signals are established due to interaction of analytes to the conductive polymer film. However, the Payne device requires high frequencies ranging from 100 MHZ to 500 MHZ, where the resonance may occur. The high frequency brings significant difficulties in instrument manufacturing and application. In addition, it still has the disadvantages inherent from polymer films.

In order to overcome deficiencies of the Payne technologies and invent a new single sensor applying frequency sweeping, the '425 Sun Patent discloses a single sensor as an analytical sensor for detecting analytes in fluids. The sensor is constructed from applying a pair of electrodes, wherein between the electrodes there are no additional materials designated to adsorb analytes if their concentrations are high, or there are adsorbents if the analyte concentrations are low. An alternating current voltage of varying frequencies is applied to the sensor by an alternating current device. In return, it detects electrical properties such as impedance and its components, reactance, resistance, and phase angles of the sensor with the analytes in fluids when they reside in or pass through the electrodes at each frequency. Thus two spectra of electrical properties of the analyte can be established at various applied frequencies from a single measurement. The electrical properties are analyzed by a pattern recognition process, and compared with those of the known objects. Therefore, the analyte can be detected and identified. A reference sensor is provided with the same configuration of the analytical sensor. By combining electrical properties from the analytical and reference sensors, the present invention provides a number of advantages, including elimination of humidity influence, polymer film aging effect, and electrical property variations caused by the temperature variations.

In the sensor instrument system development disclosed by the '333 Lewis Patent, a remote data processing function is combined with the sensor array including the carbon black polymer modified chemiresistors. Obviously, addition of the remote data processing is positive to the performance of the sensor instrument system.

However, in various situations, comprising a situation of testing air pollutants including ground level ozones in a regional environmental study, there is an additional need for a sensor instrument system which enables the sensor to provide information on variations of air pollutants in situ correlating to variations of geographic positions. Therefore, if satisfying the need, a regional pollutant distribution can be mapped for better understanding thus controlling the regional air qualities. Such capability of the sensor instrument system is also advantageous to many other studies.

Therefore, it is desirable to design and develop a new sensor instrument system including methods that overcomes the disadvantages of conventional sensor devices, and has a better reproducibility of performance and sensor manufacturing, fewer interference deficiency, enhanced sensitivity, less restricted operation conditions, and increased portability. In addition, the sensor instrument system will have wireless communication capabilities for processing data and abilities to locate geographic positions that associate with variations of the analyte information.

SUMMARY OF THE INVENTION

The present invention is directed to a system comprising a sensor instrument and a remote central station for detecting analytes in fluids. The sensor instrument includes an analytical detection module connected to a single sensor for acquiring data of the analyte electrical properties, a GPS (global positioning system) receiver module for obtaining data of the analyte geographical positions, and a data transmission module for wirelessly communicating the data to the central station. The single sensor is operated with alternating current (AC) including periodic electrical excitation signals having swept frequencies for detecting analytes in fluids. The central station after wirelessly receiving the data transmitted by the sensor instrument processes and stores information of the analytes, wherein the analyte information is incorporated with the geographic positions where the respective analytes are detected.

It is an object of the present invention sensor instrument system including method to provide a new and unique sensor configuration for detecting and identifying analytes in fluids, which utilizes a single sensor having two electrodes operated by an electrical frequency sweeping technique from a single measurement to obtain two sets of patterned AC electrical properties of an analyte at various swept frequencies including preferred frequencies ranging from 10 KHZ to 1 MHZ, wherein the electrical properties that are obtained at each frequency are governed by the natural characteristics of the analyte including the dielectric constant, polarity or dipole moment.

It is also an object of the present invention sensor instrument system to provide a new and unique sensor instrument comprising a single sensor having two electrodes operated by an electrical frequency sweeping technique for detecting and identifying analytes in fluids, wherein the analytes can be identified by comparing patterns of the respectively obtained analyte AC electrical properties with patterns of AC electrical properties of known chemicals of interest.

It is another object of the present invention sensor instrument system to provide a new and unique sensor instrument comprising a single analytical sensor having two electrodes operated by an electrical frequency sweeping technique for detecting analytes, in fluids, wherein the instrument has a background reference mechanism from employing a reference sensor having the identical electrodes as the analytical sensor to reduce influence of the background noises including humidity level, polymer film aging and electrical property variations caused by temperature variations of the respective analytes positioned between the analytical sensor electrodes and improve identification of the electrical properties contributed by the respective analytes.

It is a further object of the present invention sensor instrument system to provide a new and unique sensor instrument comprising a single sensor having two electrodes operated by an electrical frequency sweeping technique for detecting analytes in fluids, wherein the instrument employs a temperature programming including the gradient and constant temperature programming on regulating the temperature of the sensor compartment including the sensor and analytes to improve the performance of the analyte detection.

It is a further another object of the present invention sensor instrument system to provide a new and unique sensor instrument comprising a single sensor having two electrodes operated by an electrical frequency sweeping technique for detecting analytes in fluids, wherein the instrument has capabilities for applying all types of organic, inorganic, and metal adsorbent materials positioned between two electrodes to adsorb or absorb the respective analytes for improving the analyte detection.

It is a further additional object of the present invention sensor instrument system to provide a new and unique sensor instrument comprising a single sensor having two electrodes operated by an electrical frequency sweeping technique for detecting analytes in fluids, wherein the instrument is compact in size, portable, easy to use, has less background influence, is inexpensive to produce, and is low in power consumption for controlling temperature of the sensor compartment including the respective analytes positioned between the sensor electrodes.

It is also an object of the present invention sensor instrument system to provide a new and unique sensor instrument comprising at least one sensor having two electrodes operated by an electrical frequency sweeping technique for detecting analytes in fluids, wherein each of the at least one sensor is filled with different materials between the electrodes to adsorb and absorb the respective analytes, and each of the at least one sensor is electromagnetically shielded for preventing cross-talk influence caused by electromagnetic radiation of the applied swept electrical frequencies.

It is another object of the present invention sensor instrument system to provide a new and unique sensor instrument comprising at least one single sensor having two electrodes operated by an electrical frequency sweeping technique for detecting analytes in fluids, wherein each of the at least one sensor is filled with different materials between the respective electrodes to adsorb and absorb the respective analytes, and each of the at least one sensor that is electromagnetically shielded is sequentially applied by the electrical frequency sweeping excitation signals for eliminating cross-talk influence caused by electromagnetic radiation of the applied swept frequencies.

It is a further another object of the present invention sensor instrument system to provide a new and unique sensor instrument comprising at least one sensor, wherein one of the at least one sensor is the present invention single sensor having two electrodes operated by an electrical frequency sweeping technique, and rest of the at least one sensor are selected from the existing multiple sensor technologies for detecting and identifying analytes in fluids.

It is a further additional object of the present invention sensor instrument system comprising a plurality of the disclosed new and unique identical sensor instruments, which are remote from a central station. Each identical sensor instrument, which is movably positioned in the respective local area for detecting the local analytes in fluids, is comprised of a detection module connected to a single sensor operated by an AC electrical frequency sweeping technique for obtaining the AC related electrical properties of the respective analytes, a GPS receiver module for locating the local geographic positions where the respective analytes are detected, and a transmission module for wirelessly transmitting data to the central station, wherein the data comprises the obtained analyte AC electrical properties and the located analyte local geographic positions.

The central station including a central computer is through an existing network means connected to a plurality of receiving sites comprising the respective antennas, which connect to the respective transceivers. The receiving sites are positioned at the respective local areas, which are the same local areas where the respective sensor instruments are movably positioned. Therefore, the analyte data transmitted by the respective instruments through the respective local receiving sites is received by the central computer, which is installed with application software of the GPS positioning maps and application software of the analysis algorithms including the pattern recognition algorithms. In this setting, the analyte electrical information obtained at the respective local positions is analyzed at the central station by applying the algorithms to thereby identify the analytes located at the respective local geographic positions. Results of the identified analytes correlated with the respective geographic positions are stored in the central station for various applications including a mapping of the in situ analyte distribution in a region containing the plurality of the local areas.

The present invention sensor instrument system provides the novel and unique sensor instrument including methods for identifying analytes in fluids. The identification of the analytes is based on detecting various patterned AC electrical properties of the respective analytes in fluids such as current, voltage and impedance including its components: resistance, reactance and phase angle, as they are governed by the analyte chemical characteristics. The present invention utilizes a single sensor that has two paired metal conductors as the spatial electrodes or two paired metal conductors positioned on ceramic or silicon substrates as the respective thick film and thin film electrodes to measure AC related electrical properties of the respective analytes residing or passing between the metal electrodes at various swept electrical frequencies comprising the preferred frequencies ranging from 10 KHz to 1 MHZ.

The measurement results in two sets of patterned AC electrical properties for each of the analytes at the applied swept frequencies. Applying a pattern recognition procedure, patterns of the AC electrical properties of the respective analytes can be recognized. Therefore, the analytes can be identified by comparing the respective recognized patterns with patterns of the electrical properties of known analytes of interest.

As discussed, the identification of analytes in fluids from the present invention is based on generating various patterned AC electrical properties gathered from the respective analytes being tested, which properties are specific to the respective analytes and are gathered from various dimensions. Therefore, the present invention is focused on finding such specific characteristic electrical properties that are related to the natural characteristics of the respective analytes, which can be measured simultaneously by a technique.

For example, the dielectric constant is one of the natural characteristics of a chemical being the analyte of interest, which is in one dimension to describe the analyte. Thus the dielectric constant can be used to identify the analyte. The dielectric constant can be measured in the AC electricity as the capacitive reactance, which is a predominant part of the reactance for short electrodes. Therefore, the reactance is a good approximation for the reactive capacitance, wherein the reactance can be measured from an impedance complex in the vector domain. Hence, the reactance is one of the specific AC electrical properties of the analyte, and is also in one dimension useful for detecting and identifying the analyte from the present invention (in the scalar domain, capacitance is proportional to the dielectric constant and has been used for identifying chemicals, see the Balters Publication). Therefore, analytes can be detected and identified according to the respective values of the analyte reactance.

In addition, regarding an analyte being a gaseous mixture, the dielectric constant of mixed gases can be estimated according to several methods. For example, the dielectric constant of the natural gas mixture is calculated as a function of temperature, density and composition of the mixture (Harvey, A. H.; Lemmon, E. W.; Method For Estimating The Dielectric Constant of Natural Gas Mixtures, *International Journal of Thermophysics*, Vol. 26, No. 1, 31-46, January 2005). The authors state that their method is better than the traditional mixing rule. Regarding an analyte being a liquid mixture, the dielectric constant of mixed liquid can be measured, which can be further explained according to the Clausius Mosotti theory, or the Onsager theory (Sen, A. D.; Anicich, V. G.; Arakelian; T; Dielectric Constant of Liquid Alkanes And Hydrocarbon Mixtures, *J Phys. D: Appl. Phys.* 25 516-521).

It will be appreciated, from the above listed research, the dielectric constants still serve as the characteristics of the respective gaseous and liquid chemical mixtures. Therefore, the present invention can use the reactance, to detect and identify the respective analytes of the chemical mixture in the respective gas and liquid phases.

Besides its dielectric constant, the chemical of the analyte has its unique composition of chemical elements having the respective characteristic electronegativities to thereby form the chemical specific molecular dipole moment or polarity, which is another natural characteristics of the chemical. Such characteristics may be measured by resistance. For example, volatile organic chemicals including those rich in hydrogen and oxygen change electrical conductivity (resistivity) of metal oxide based sensors (see the Nagle and Balter Publications), wherein hydrogen and oxygen have the respective large electronegativities.

It will be appreciated that, the resistance in the AC electricity can also be simultaneously measured as another component of the impedance complex, as compared with the measured reactance, wherein the reactance is the dominant component in impedance comparing with resistance since an analyte in pure form (including the gas phase) is not electrically conductive. However, although the resistance value is small, it reflects resistive characteristics of the analyte and describes the analyte in another dimension of the chemical natural characteristics, which is orthogonal to the dimension of the reactance. Therefore, the resistance information is also important for identifying the analyte.

With varying the frequencies, the present invention enables obtaining two sets of the patterned AC electrical properties such as resistance and reactance for an analyte, so as to the respective analytes for detection and identification purposes.

Impedance that is the summation of resistance and reactance including the capacitive reactance can be obtained applying Ohm's law in AC electricity:

$$Z = V/I \quad [1]$$

where Z is the impedance vector, V is the voltage vector, and I is the current vector. It can be understood that from the above equation, the voltage across the sensor is proportional to the impedance under a constant current technique. Current passing through the sensor electrodes is reverse proportional to the impedance applying a constant voltage technology. Therefore, as alternatives, either current or voltage can be used (in the place of impedance) for detection and identification purpose.

The present invention sensor instrument system including method does not require additional materials positioned in the sensor electrodes for adsorbing analytes with sufficient concentrations. When the analyte concentrations are insufficient, the present invention has the option of using adsorbent materials in the sensor design to selectively adsorb or absorb analytes for improving sensitivity and detection limit of the sensor.

Obviously, the dimensions of the respective resistance and reactance from the sensor electrodes filled with adsorbent materials are different from those of the resistance and reactance of the sensor electrodes without having the materials. It is because the single sensor filled with the adsorbent materials will record the AC electrical properties of a particular chemical or chemicals of an analyte in a fluid, wherein the respective chemical or chemicals are adsorbed by the adsorbent materials due to specific interactions among the chemical or chemicals and the materials.

Therefore, having the spirit and scope of finding characteristic dimensions of the respective analytes, the present invention enables the filling of the adsorbent materials in between the sensor electrodes for detection and identification of the analytes in fluids even the analyte concentrations are sufficient.

It will be appreciated that adsorption process can associate with absorption process, or the adsorption and absorption precesses can be happened simultaneously to thereby be the sorption process. However, the exact situation regarding a specific process will be dependent upon facts including types of the materials, sizes including thickness of the materials added between electrodes, allowed times for the adsorption process, and amount of the analyte in analysis. Therefore, the adsorption disclosed herein may include absorption or sorption.

The sensor instrument of the present invention, which is movably used in a local area, is an integrated one. The instrument is structurally comprised of eight modules including a sample handling module, a sensor compartment module attached by an exterior heater of a heating module, a detection module, a microcomputer module, a data transmission module, a GPS receiver module, and a power module. The detection module is comprised of an analog circuit section acting as a detector connected to an interface such as an analog-to-digital converter (ADC), which is further connected to the microcomputer module that is a miniaturized personal computer. Therefore, all other modules can through the respective interfaces if necessary connect to the microcomputer module. In addition, the microcomputer module is installed with a first application software comprising the GPS positioning maps, and a second software comprising analysis algorithms including the pattern recognition algorithms, so that the detected electrical information can be analyzed locally by the sensor instrument. The analysis results in identification of analytes in fluids. Further the identification results can be transmitted to the central station, which is an additional structure of the present invention sensor instrument system.

Accompanying with the local sensor instrument, the present invention includes the central station comprising a central computer connected to a server computer, with one of its functions used for storage of the digital information. The central station connects to an existing network means, which is connected to a plurality of local receiving sites positioned in a region having multiple local areas. The network means is comprised of an Ethernet, an intranet, the internet, and the Internet linked by fiber-optical cables, metal wires and wireless connection including the electromagnetic waves.

Each identical local receiving site is comprised of an antenna connected to a transceiver, which is connected to a digital data acquisition module having a CPU. Therefore, the data transmitted from the local instrument can be received by a receiving site positioned at the same local area as the instrument positioned, since the instrument and the receiving site have the same transmission protocol. In this setting, the data of the analyte electrical information and analyte geographic position in a local area can be transferred to the remote central station.

The central computer is installed with the same first application software comprising the GPS positioning maps and the second application software comprising analysis algorithms including the pattern recognition algorithms. Therefore, the analyte electrical information can either be processed locally at the sensor instrument or remotely at the central station after the information is wirelessly and remotely received.

It will be appreciated that, the disclosed "computer" herein including microcomputer, central computer and server computer is comprised of all required basic components, according to a common knowledge in electrical engineering so that they are operable including having a data storage function. The word "connected" means electrical connection, so that electricity including the digitized electricity in the form of codes, data, instructions and programs can flow within a device including the sensor instrument, the central station connected to the local receiving site through the network means.

The present invention sensor instrument including method has many novel and unique features and advantages for detecting and identifying analytes in fluids. In summary, the core technology utilizes a single sensor operated with the frequency sweeping technique at various swept frequencies. Therefore, two sets of the patterned characteristic electrical properties can be obtained with a single measurement, wherein electrical properties including the resistance and reactance can be simultaneously obtained at each of the swept frequencies. The resistance and reactance are in two orthogonal dimensions over the time (frequency) to describe the analyte characteristics, which is a significant advantage of the present invention, as compared with one dimension of detection over the time from the existing multiple sensor technologies. The preferred frequencies range under 1 MHZ, which results in an easy instrument design and application. It does not require the use of conductive polymer film or conductive polymer composite in the sensor structure and has capability to apply all types of adsorbent including absorbent materials.

The sensor instrument also provides a reference sensor for compensating background influence. In addition, the instrument uses a temperature programming including the gradient and constant temperature programming to the sensor compartment containing the sensor and an analyte in a fluid for better controlling the adsorption and desorption processes of the analyte, which improves the analyte detection and identification. In addition, the present invention has a low cost to manufacture the sensor instrument, which is compact in size to make it portable and easy to use.

These advantages particularly benefit a handheld sensor instrument powered by DC batteries, due to a small size of the single sensor that results in a low power consumption to control temperature of a small sensor compartment.

It will be appreciated that one of the main advantages of the present invention is to use a sensor from the single sensor strategy for generating two spectra of the respective patterned AC electrical properties of an analyte at the same time from a single measurement. The reproducibility of manufacturing the sensors can be easily achieved with the present single sensor strategy when a few pairs of the identical sensors are needed for constructing the sensor instrument. The small size which results in low power consumption for controlling sensor compartment temperature and small volume requirement also allow the practical implementation of a dual sensor strategy which, in addition to an analytical sensor, incorporates a reference sensor having the identical configuration as the analytical sensor.

With the dual sensor strategy, samples of analytes in fluids with background subjects such as humidity levels are tested by the analytical sensor while only the background subjects including the fluids are tested by the reference sensor. By comparing the outputs from the analytical and reference sensors, the background effect can be removed from the test results of the respective analytes. Similarly, as the additional background, the aging effect of the polymer films dispensed in sensors, and changes in the testing responses induced by the temperature variations, can also be removed or eliminated. Furthermore, application of the dual sensor strategy brings an additional advantage of increasing the testing speed since testing of the analytical and reference sensors is completed simultaneously.

In addition, with the incorporation of existing technologies of the wireless data transmitting, and geographic position locating through application of the global positioning system (GPS), the present invention sensor instrument system including method enables providing in situ information of the analyte distribution in a region when applying a plurality of the sensor instruments in study of analytes positioned at the respective local areas of the region.

It will be appreciated that, besides the GPS established in the United States of America, several other similar systems are in processes of construction worldwide. Therefore, from the spirit and scope of locating the analyte geographic positions, the present invention comprises application of any geographic positioning system as long as it is available for use in public.

These and further novel features and objects of the present invention will become more apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 4A shows the dual sensor 12 without an integrated form of two sensors;

FIG. 4B shows an integrated form 13;

FIG. 6 shows a schematic of any type of adsorbent materials 8 placed onto electrodes or a capacitor for adsorbing analytes in fluids;

FIG. 7A shows a schematic diagram to illustrate a different configuration 4 to form a single sensor, where an electrode acting as a first electrode and electrically conductive structure member such as a sidewall acting as a second electrode;

FIG. 7B shows a sidewall is properly grounded in connection of the sensor 4 to the alternating current analyzing device 9;

FIG. 10 shows a transverse cross sectional view of the middle section of the sensor compartment as illustrated in FIG. 9;

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 3:
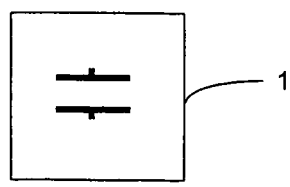
FIG. 3 illustrates a schematic diagram of a single sensor 1 containing a pair of metal wires or plates acting as electrodes or a capacitor.
Figure 5:
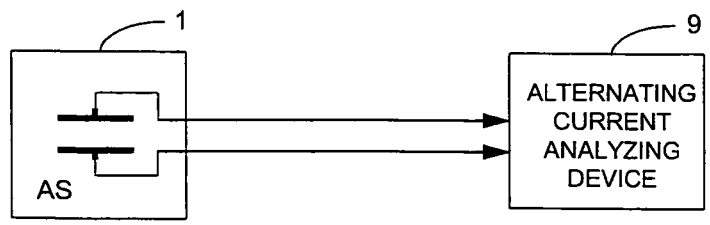
FIG. 5 shows a diagram for electrically connecting a single sensor 1 to an alternating current analyzing device 9.

The present invention sensor instrument system including method for detecting and identifying analytes in fluids has three main objectives. Referring to FIGS. 3 and 5, the first major objective is to design a sensor 1 having two electrodes from a single sensor strategy for a single sensor 1) for effective identification of an analyte in a fluid by detecting certain electrical properties which are associated with the analyte's distinguished physical and chemical characteristics, such as dielectric constant, element electronegativity, and polarity or dipole moment.

This first main objective of the present invention is achieved by applying an electrical frequency sweeping, which is acquired from an alternating current (AC) analyzing device 9 connected to the single sensor 1 containing the analyte. Therefore, it obtains two sets of the patterned analyte AC electrical properties according to various swept frequencies from a single measurement, wherein the electrical properties are obtained at each frequency. In this setting, various analytes can be detected. By analyzing the obtained electrical properties of the respective analytes with a pattern recognition process, patterns of the respective analyte electrical properties can be recognized, which are correlated to the respective analytes. Therefore, each of the analytes can be identified by comparing the recognized pattern of the analyte with patterns of known substances. It will be appreciated that the first object reflects a core technology of the present invention.

Figure 4A:
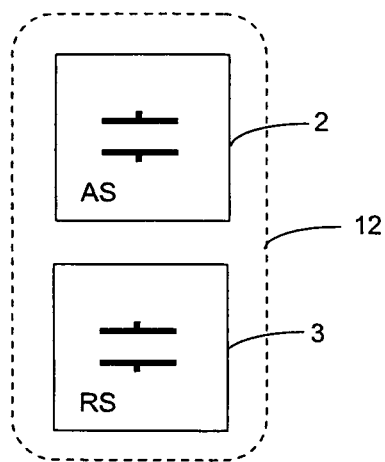
FIG. 4A shows a dual sensor which utilizes two identical sensors 1, one as an analytical sensor 2 (AS in abbreviation), and the other as a reference sensor 3 (RS).
Figure 4B:
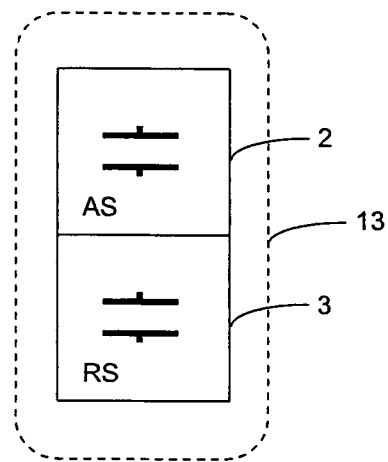
FIG. 4B shows a dual sensor which utilizes two identical sensors, one as an analytical sensor 2, and the other as a reference sensor 3.

The second main objective of the present invention is to provide a sensor strategy including a method that can eliminate background influence, including humidity level, polymer edging effect and variations of the analyte electrical properties caused by the temperature variations. Referring to FIGS. 4A and 4B, the second main objective is achieved by applying a dual sensor strategy which utilizes a dual sensor having two identical sensors 1, one as an analytical sensor 2 and the other as a reference sensor 3. The dual sensor has two embodiments, an integrated one 13 and another separated one 12. Alternatively, the present invention dual sensor strategy can be used to identify electrical properties of a chemical or chemicals of an analyte that is a chemical mixture. The strategy is particularly useful to test a biochemical marker or markers from a biological sample for medical diagnoses.

It will be appreciated that implementation of the dual sensor strategy is practically applicable in the present invention due to the advantage of the small volume of the analytical sensor that can generate two sets of the patterned information for an analyte in fluid in a single measurement.

The third main object is of incorporating the existing wireless data communicating and GPS positioning technologies with the present invention core technology to form the sensor instrument system. The system is comprised of a central station positioned remotely to a plurality of identical sensor instruments positioned at the respective local areas of a region. The identical sensor instrument is configured, comprising a detection module, a GPS receiver module and a data transmission module. The central station connects to the network means, which further connects to a plurality of identical local data receiving sites positioned at the respective local areas of the region. Therefore, one local sensor instrument can transmit the detected analyte information and the located geographic position of an analyte where it is detected to a local receiving site that is positioned at the same local area as compared with the analyte, so that the analyte electrical information along with the analyte geographic position can be received and identified by the central station. In this setting, analytes of the region can be remotely detected and identified, which can further result in an in situ mapping of distribution of the analytes in the region.

Disclosure of the present invention includes two sections. The first section introduces the core technology of the present invention: the single sensor operated by AC excitation signals having swept frequencies. The second section introduces implementation of the existing knowledge of wirelessly transmitting data and GPS locating positions to the core technology, which forms the present invention sensor instrument system.

In the present invention sensor instrument system including method, an analyte of interest refers to a chemical having a plurality of molecules with the same molecular formula. The analyte also refers to a specific mixture of different chemicals that are grouped together, wherein each chemical has a plurality of molecules have the same molecular formula, for example, the chemical mixture of a coffee smell. The analyte may not have an odor, such as a chemical of hydrogen, or a mixture of the industrially produced combustive gases without addition of the smell substance. The analyte also may have an odor, for example, as a chemical of acetic acid, or mixed chemicals in perfumes a smell of a bad breath from a living object, or a smell of sewerage. Analytes refer to a plurality of the respective different chemicals or chemical mixtures. The analyte or analytes are in gaseous or liquid phases.

In general, the chemical analytes as the interest of this study can be from materials containing illegal substances (comprising marijuana), environment concerns (comprising air, water and soil pollutant monitoring such as ground level ozones in the air), medical interests including hospital concerns (comprising biological sample including breath analysis), scientific and research interests including space research interests (comprising study of air quality in space vehicles), interests of industrial sectors including food (comprising freshness testing of meat and fish), beverages (comprising order testing of lemonade), agricultural (comprising testing of fruit ripeness), chemical (comprising monitoring of hydrogen chloride production), petroleum (comprising flammable gas leakage detection), plastic (comprising process and quality control), construction (comprising indoor air monitoring for newly built buildings), pharmaceutical (comprising new drug discovery), automobile (comprising lubricating oil and fluid monitoring), biochemical (comprising biochemical syntheses including from enzyme-catalyzed reactions), and transportation (comprising emission control), consumer interests including perfume, cosmetic, wine and flavor, safety interests (comprising explosive, arson, and road spill investigation) and military interests (chemicals used as weapons).

The fluid in this disclosure refers to a chemical background in either gaseous or liquid phases, which is not of interest in the study. The fluid serves to "host" the analyte or analytes. In a pure condition of the analyte in the fluid, the analyte itself can serve as the fluid. In a situation when the analyte and fluid are mixed together, a fluid can either be a chemical or a chemical mixture. For example, in the case of studying air pollutants, the air that is a mixture of various gases is the fluid to host the gaseous pollutants. In the case of a GC, the hydrogen or nitrogen or helium as a carrier gas serves as the fluid to carry out various separated chemicals that is originally of a chemical mixture.

Fluids refer to a plurality of the respective different chemicals or chemical mixtures. For example, in a study of bad breath caused by dental diseases for a plurality of patients, a biochemical marker gas of hydrogen sulfide is the analyte of interest, which is common to all the patients' breath samples. Obviously besides the marker gas, a breath sample from a patient is comprised of additional chemical gases that are not the interest of study, which are referred to a fluid. However, compositions of additional chemical gases are different for different patients. Such as, percentages of the respective produced carbon dioxide and unconsumed oxygen, which are part of the additional chemical gases of the breath, are dependent upon each patient's health conditions including the lung function and the blood system function. Therefore, the breath samples of all patients, which are tested, have the same marker gas but different fluids. In this situation, it refers to a sample group as "an analyte in fluids" of this disclosure.

Following the above analogy, in study of patients' breath samples for medical diagnoses of different organ diseases such as lung, kidney and intestine diseases, the breath samples are comprised of the respective different marker gases as the study interests in the respective different fluids. This refers to "analytes in fluids" of disclosure.

Opposite to the above defined sample group "analyte in fluids", there is a sample group "analytes in a fluid". For example, a same carrier gas (or solvent) serves as a continuous fluid to host different chemicals, which are separated in the gas (or liquid) chromatographic process from an initial analyte that is a chemical mixture. Another example is from a regional air pollution case, where the same air hosts various different pollutants according to different areas of the region. It will be appreciated that, the case of "analytes in fluid" in the chromatographic process is a special one, wherein it is the process that separates an initial analyte of a chemical mixture into various analytes of the respective chemicals in series, which are separately positioned in the same fluid to thereby are individually detected.

However, it will be appreciated that, no matter of what kinds of sample groups in studies of the analyte detection and identification, each sample must be sequentially tested by the sensor instrument. Therefore, for a general disclosure of testing the above defined sample groups: "analytes in fluid", "analyte in fluids" and "analytes in fluids", it comprises the sequential steps of testing, where each individual sample is sequentially tested. Regarding each tested individual sample at a testing moment, it only contains an analyte in a fluid according to the above defined analytes and fluids.

Chemicals are well known to have the respective distinguished dielectric constants. They also contain various chemical elements that have the respective distinguished electronegativities. In addition, at a molecular level, chemicals have the respective unique molecular structure, sizes, weights, shapes including symmetries, and dipole moments. These factors determine physical and chemical characteristics for the chemical analytes, and affect the adsorption and desorption processes of the respective chemical analytes interacting with sensor electrodes.

These physical and chemical characteristics can be described with certain AC electrical properties of the respective analytes, such as, current, voltage and impedance Z including the phase sensitive components: reactance X, resistance R, and phase angle $\theta$, as the respective analytes are excited by an AC signal at a frequency. The AC excitation signal herein refers to an alternating current or voltage in the form of sinusoidal waves.

Referring to FIG. 5, the AC electrical properties can be obtained by using an instrument impedance analyzer or any other known alternating current analyzing device 9 connected to the single sensor 1. In its simplest form, the single sensor 1 as the test device can be a pair of metal wires or plates acting as spatial electrodes or a capacitor. The paired electrodes of the single sensor can also be positioned onto the respective ceramic and silicon substrates to be the respective thick and thin film electrodes according to the industrial terminology of manufacturing the electrodes. The thick and thin firm electrodes can be alternatively defined as the electrodes positioned onto the respective ceramic and silicon substrates. The AC electrical properties, as detectable information of an analyte present in a fluid, are obtained as it resides or passes between the electrodes or capacitor.

Impedance is described as $$Z=R+X \quad [2]$$

in complex (with the bold letters indicating vectors). The phase angel $\theta$ can be calculated from the R and X values.

Reactance X of the sensor of the present invention is combined with a reactive capacitance $X_C$, and reactive inductance $X_L$, which can be described as follows:

$$X_C=j(-1/2\pi fC) \quad [3]$$

$$X_L=j(2\pi fL) \quad [4]$$

where C is a capacitance that is proportional to a dielectric constant of a medium residing between electrodes, and L is the inductance of the electrode. For a short electrode of the present invention, the value of inductance L is small and the reactance X is predominantly capacitive. Thus the reactive capacitance $X_C$ is a good approximation of the reactance X.

Therefore, if in the presence of an analyte in a fluid between the electrodes, the reactance is X(2). If in the absence of the analyte the reactance is X(1), which is the contribution of the fluid, then their difference $\Delta X$:

$$\Delta X=X(2)-X(1) \quad [5]$$

can be obtained, which is change of the reactance as the electrical contribution of the presented analyte.

Since the capacitance of the analyte is governed by the dielectric constant and the reactive capacitance is predominant of the reactance, the reactance can be used to detect and identify the analyte. This means reactance provides a signature information of each chemical or chemical mixture. By varying the frequencies in a single measurement, the present invention is able to construct a reactance spectrum to record chemical characteristics of the analyte at each of the swept frequencies. Therefore, the spectrum contains a series of the analyte patterned AC related electrical properties.

Analytes will be adsorbed by surface of the test device through the chemisorption and physisorption processes. This capability creates a complicated diffusive process, and surface interfacial kinetics or surface resistance for the analytes, which are associated with their distinguished molecular characteristics. For example, exposure to volatile organic compounds including those rich in hydrogen or oxygen noticeably changes the electrical conductivity of metal oxide sensors (see the Nagle and Blaster Publications).

Since each chemical element of analytes such as oxygen or hydrogen or nitrogen or carbon has its defined electronegativity, which contributes the polarities or dipole moments of the respective analytes, the change of conductivity (resistivity) indicates that resistance can be used to record chemical characteristics of the respective analytes In the present invention, a series of resistance information is also simultaneously generated with varying frequencies in the same single measurement, where the reactance information is obtained. The change of resistance at each frequency is defined as:

$$\Delta R=R(2)-R(1) \quad [6]$$

where R(1) is the resistance of a fluid in the absence of any analyte and R(2) is the resistance of the electrodes exposed to an analyte in the fluid. The change of resistance is the contribution of the analyte.

Comparing magnitude of resistance and reactance of an analyte, it will be appreciated that reactance is predominant over the resistance, which governs values of impedance since the analyte in the fluid is not conducting in the dry condition. It will be also appreciated that phase angles $\theta$ can be calculated from R and X. Therefore, the change of phase angle $\theta$ is also readily available. Combining the information of change of reactance and resistance and/or change of phase angle at each frequency, a plot of containing curves of the respective reactance, resistance and phase angle is constructed over the swept frequencies, which shows a patterned electrical information of the analyte. Therefore, in a general practice, the plotted curves of the analyte can be first studied for their characteristics including through comparison with curves of known analytes that have been already established in a database, so that the characteristics including similarity, or dissimilarity, or a pattern of the electrical information of the analyte may be recognized through directly analyzing the plotted curves.

Following the above disclosed processes, a plurality of different analytes can be tested, which results in obtaining a plurality of the respective patterned analyte AC electrical properties.

Beside the plotted curves which are in a continuous data form of the patterned analyte electrical properties, a discrete data form of the properties can also be established by constructing a matrix of the analyte characteristic electrical properties. The matrix comprises an even number of columns, wherein each two adjacent columns are for inputting the respective analyte electrical properties at one frequency, for example reactance and resistance data. Therefore, the matrix has a maximum number of the columns, which is twice of the number of the swept frequencies (see specification of the commercial analyzing device on the number of collected frequencies). Or, the column number can be dependent upon a number of frequencies that are randomly or specifically selected within the swept frequencies. A row represents obtained electrical properties of one measured analyte according to the listed frequencies in the matrix. Obviously, the same analyte can be measured multiple times in the experiment.

Following the above disclosed procedure, a matrix can be established for a plurality of analytes, wherein one row represents obtained electrical properties of one of the analytes according to the selected frequencies if each of the analytes is measured one time.

As the change of the AC electrical properties, which varies nonlinearly with varying frequencies, variations of the characteristic electrical property changes, which are presented in the matrix for the tested analytes, can be analyzed through application of various known analysis algorithms, which comprise multivariate analysis method that includes various pattern recognition algorithms. Applying such analysis including pattern recognition analysis on the matrix of the analyte electrical properties, characteristics including patterns of the respective analytes can be easily recognized, as compared with the difficulty in finding patterns through directly analyzing the plotted curves of the respective analytes.

As a result, an analyte can be identified by comparing the recognized pattern of the characteristic electrical properties of the analyte with patterns of known substance from a database that has been already established.

It will be appreciated that, although the preferred frequencies of the present invention are swept from 10 KHz to 1 MHz, other frequencies, which are different from the preferred frequencies, can also be applied according to the principle and scope of the present invention. However, applying the preferred frequencies can not only identify the analytes but also increase the options of instrument design and practical application.

The present invention sensor design does not require the use of any conductive polymer film for detecting or identifying analytes at sufficient concentrations. This is because the AC excitation signals can be applied across the vacuum, thus they can be across the gap of the two electrodes without conductive materials placed in between. This is suitable to be used as a detection of the chromatographic methods including GC and LC (a liquid chromatography), where each chemical of the chemical mixture is separated and concentrated in the chromatographic process. This new detection method will provide information on not only the quantities but also the identities of the analytes. Besides, this new detection is non-destructive, which is an additional advantage.

In addition, referring to FIG. 6, since AC signals can travel through vacuum, the present invention can use any type of adsorbent or absorbent or sorbent materials 8, whether or not they are electrically conductive, for detecting analytes in fluids from concentrating or selectively concentrating dilute analytes. Thus the present invention can utilize a variety of developed and known techniques on concentrating analytes or selectively concentrating chemical marker or markers of the respective analytes in fluids to improve sensitivities and selectivities of the sensors. Such techniques typically involve application of polymer films, polymer inorganic materials composites, composites containing particles of the platinum group metals, solid inorganic materials used as stationary phase in the gas adsorption chromatography, and polymeric materials used as stationary phase in preparation of packed and open tubular columns in the gas partition chromatography.

For example, hydrogen is an important industrial gas for many applications. It is often critical to detect and identify the hydrogen gas for safety concerns. In the present invention, the hydrogen gas can be selectively concentrated by applying composites containing palladium particles, composited by organic or inorganic fillers. This is because the hydrogen gas has a large solubility in the palladium metal that can absorb up to 900 times its own volume of hydrogen (Hand Book Of Chemistry And Physics, CRC Press, 24th Edition, 4-21, 1993-1994). For this reason, palladium is often referred to as a "hydrogen sinker". Since the analyte detection of the present invention is not limited to the adsorbent materials that are electrically conductive, it has a great flexibility to choose any percentage of palladium metal including the particle form in the composite, according to concentration of the hydrogen gas in fluid, to concentrate and then detect the hydrogen gas in the application of the present invention.

In addition, palladium is one of the platinum group metals, consisting of ruthenium, rhodium, palladium, osmium, iridium and platinum. They have similar physical and chemical properties including the hydrogen solubility (Hand Book Of Chemistry And Physics, CRC Press, 24th Edition, 4-15 to 4-25, 1993-1994). Therefore, each metal of the platinum metal group is appropriate in the application of the present invention.

Furthermore, the gas adsorption chromatography uses solid particles as stationary phase to selectively adsorb molecules. Various solid inorganic materials can be used for this purpose. Among them, molecular sieves, silica gel, alumina, glass, porous carbon particles, and calcium carbonate are the most popular choices. In addition, fluorocarbon powders are also appropriate, such as tetrafluoroethylene polymer particles. Illustration of these basic materials can be found elsewhere (Poole, C. F.; Poole, S. K.; Chromatography Today, 199-209, Elsevier Science Publishers. B. V., 1991, and references cited therein).

For example, molecular sieves are materials containing fine pores of precise and uniform sizes, which can be controlled in manufacturing. The molecular sieves have been known and used as the adsorbent materials for gases and liquids. They retain adsorbates by strong physical forces, and separate molecules based on their sizes, configurations, polarities, and degrees of unsaturation. Molecular sieves will adsorb carbon monoxide in preference to argon. They preferentially adsorb polar molecules containing oxygen, sulfur, chlorine, or nitrogen atoms, and asymmetrical molecules containing oxygen, sulfur, chlorine, or nitrogen atoms, and other asymmetrical molecules. Molecular sieves also effectively retain water and carbon dioxide and trap ethylene or propylene from saturated hydrocarbons.

In gas partition chromatography (GC), separation of chemicals in a mixture is based on vapor pressures of the respective chemicals and selective interactions between the respective chemicals and polymeric materials used as the stationary phase of the GC columns. The stationary phase materials are coated onto the solid support particles for the packed columns or the interior surfaces of the open tubular silica capillary columns. At the molecular level, the interaction is based on intermolecular forces between each chemical and materials of the stationary phase such as dispersion, induction, orientation, and donor-acceptor interaction. To help the understanding of the processes described above, a term "like dissolves like" may be useful to explain results of such intermolecular interactions. Selectivity is one of results of the interactions due to a similarity between "likeness" of a kind of chemicals and materials of the stationary phase of the column. For example, polarities are characteristic parameters for the respective chemicals and thus can be used to describe such likeness. Polar chemicals like polar materials of the stationary phase, and non polar chemicals go to non polar stationary phase.

Based on this principle, objective of selective partition of a series of chemicals can be achieved by using a kind of stationary phase materials whose polarities are similar to or match the polarities of the respective chemicals. For example, polysiloxane is well known as a nonpolar material. It is most popularly used as the base materials of the GC stationary phase since its basic chemical structure can be readily derived by methyl, vinyl, phenyl, diphenyl, 3,3,3,-trifluoropropyl, 2-cyanoethyl, or 3-cyanopropyl constituents to change its polarity from non polar to polar, which is known elsewhere (Poole, C. F.; Poole, S. K.; Chromatography Today, Chapter 2, 105-229, Elsevier Science Publishers. B.V., 1991, and references cited therein Hyver, K. J., Editor; Sandra, P., Guest Author; High Resolution Gas Chromatography, 2-1 to 2-16, $3^{rd}$ Edition, Hewlett-Packard Co., 1989, and references cited therein). Therefore, specifically derived polysiloxane polymers are appropriate to many types of chemicals in terms of similarity of their polarities.

The following are examples of the well known derived polysiloxane polymers that are often involved in applications of selectively partitioning various chemicals in fluid:

1. Poly(100% dimethylsiloxane) for analytes of solvents, petroleum products, fuel, oil, hydrocarbons, pharmaceuticals, flavors, fragrances, sulfide compounds, and PCBs.
2. Polymers containing (5% diphenyl/95% dimethyl), or (35% diphenyl/65% dimentyl), or (14% cyanopropyl/86% dimethyl) for analytes of pesticides, aromatic hydrocarbons, polychlorinated biphenyl, oxygenates, amines, essential oil, pharmaceuticals, environmental samples, and nitrogen containing chemicals including herbicides.
3. Poly(20% diphenyl/80% dimethylsiloxane) for analytes of flavor aromatics and alcoholic beverage.
4. Polymers containing (50% phenyl/50% methyl) or (trifluoropropylmethyl) for analytes of environmental chemicals, solvents, ketones, drugs, steroids, glycols and halogenated compounds.
5. Ploy(65% diphenyl/35% dimethylsiloxane) for analytes of phenols and fatty acids.
6. Poly(50% cyanopropylmethyl/50% phenylmethylsiloxane) for analytes of carbohydrates and neutral sterols.

It will be appreciated that, as above illustrated, the derived polysiloxane can selectively interact various chemicals of interest including the amines. The amines including the derivatives have been reported by many researchers as the targeted biochemical markers of patients' specimens including the breath samples from the medical diagnoses of many diseases. Some of the research results are listed in the '333 Lewis Patent, which are incorporated herein by references in the entirety for simplifying disclosure of the present invention.

Besides the derived polysiloxane, the meta-linked poly (phenyl ethers), phthalate ester, polyester, polyethers such as poly(ethylene glycols) and liquid organic salts are also popularly used in GC for interacting chemicals having the respective polarities. For example, poly(ethylene glycols) is a polar phase, which is particularly for analysis of acids, alcohols, aldehydes, acrylates, nitrites, ketones, essential oils, glycols and solvents. The liquid organic salts are polar, comprising organoammonium or organophosphonium cations coupled with nucleophilic anions such as sulfonates or inorganic anions such as chlorides, bromides and nitrates. Examples are tetrabutylammonium sulfonate and tetrabutylphosphonium nitrate (Poole, C. F.; Poole, S. K.; Chromatography Today, 114-118, and references cited therein; Hyver, K. J.; Sandra, P.; High Resolution Gas Chromatography, 2-9).

Polymers including the above disclosed derived polymers can be coated onto solid support particles for preparation of the packed columns or onto the interior surfaces of silica capillary columns with the existing procedures that are known elsewhere. Before coating the polymers to the solid support particles or the interior surfaces of the silica capillary columns, deactivation is a common preparation procedure for treating surfaces of the packing particles or the interior surfaces of the capillary columns, wherein the deactivation is performed to maintain or enhance the wettability of the surfaces for achieving uniform polymer firms coated on the surfaces, which is also known elsewhere.

In general deactivation is conducted by converting surface silanol groups of the solid support particles or silica columns to silyl ethers by reaction with dimethyldichlorosilane (DMCS), hexamethyldisilazane (HMDS), trimethylchlorosilane (TMCS), or a combination of these reagents, and octadecyldimethylchlorosilane (Poole, C. F.; Poole, S. K; Chromatography Today, 122-123, 137-148, and references cited therein).

It will be appreciated that, it is also popular for chemical modification of solid support particles or fused silica capillary columns to form bonded phases in GC column manufacturing. One approach involves reaction of monofunctional or multifunctional alkylsilane or cyclosiloxane reagent with silica or diatomaceous support particles or fused silica columns. In the reaction, chemical attachment via formation of siloxane bonds and polymerization are probably both involved in bonding the stationary phase to the support particles or columns. Another one includes application of peroxide-induced or ozone-induced free radical crosslinking reaction of coated packings to form immobilized polysiloxane phases. For example, moderately polar polysiloxane phases are prepared with various amounts of vinyl, tolyl or octyl groups, which increase formation of the crosslinking polymer (Poole; C. F.; Poole, S. K.; Chromatography Today, 122-127, 132-152 and references cited therein).

Therefore, it will be appreciated that the present invention can apply the above disclosed successful known techniques to treat the surfaces of the ceramic or silicon substrates of the respective thick film or thin film electrodes of the single sensor 1, or the solid support particles for use in the spatial electrodes, so that uniform polymer films can be achieved in the present invention.

Applying a single sensor with AC electrical frequency sweeping technique, the present invention can not only obtain a patterned information of each analyte but also gain a distinct advantage of having small sizes of the respective sensor and sensor compartment in sensor design. The small sizes of the respective sensor and its compartment make the present invention practically capable of utilizing a dual sensor strategy in the sensor manufacturing, particularly for manufacturing handheld and battery powered electronic nose instruments.

In the dual sensor strategy, the present invention applies a dual sensor having two identical sensors, one serving as an analytical sensor and another one as a reference sensor. When background subjects, such as humidity, are critical factors that affect sensor performance, an analyte in a fluid with background subjects are tested with the analytical sensor, but only the fluid and background subjects are tested with the reference sensor. By subtracting electrical properties of the analytical sensor from those of the reference sensor, the influence of background subjects, including humidity, can be eliminated. Therefore, the information of the analyte can be obtained without the errors introduced by the background subjects.

One application of the this dual sensor arrangement is for in situ medical diagnoses of patients, for example detecting patient ear and mouth diseases. In such diagnoses, analytes of chemical vapors generated by bacteria caused by diseases are overlapped by the humidity in breath samples, where the water concentration in humidity is significantly higher than that of the analytes. Therefore, the present invention can remove the humidity influence during testing the breath samples.

Applying the dual sensor strategy to eliminate including humidity influence for testing breath samples, the present invention can effectively detect and identify analytes by selectively detecting the respective volatile chemicals that serve as the respective biochemical markers of various diseases for medical diagnoses. This strategy of medical diagnoses is based on established correlation of biochemical markers and the respective organ diseases. In this study, an analyte is generally a chemical mixture, comprising one or several biochemical markers among various chemicals in the analyte.

Applying this strategy, a sample having an analyte in fluid with background subjects are tested with the analytical sensor. But only the background subjects and analyte without the marker(s) in the fluid are tested with the reference sensor, which is after removing the marker(s) of the analyte from application of appropriate adsorbent materials to selectively trap the marker(s) prior to measure the reference sensor (see FIG. 10). By subtracting electrical properties of the analytical sensor from those of the reference sensor, only the biomarker electrical information can be obtained.

The following sets forth some published bio-markers of diseases for medical diagnoses:

(1) Methylamine for the kidney and liver diseases, a news report of Feb. 25, 2008, Bio-Medicine, an online of organization to report results of researchers at a joint institute of National Institute of Standard and Technology and University of Colorado at Boulder USA (hereafter "BioMed);

(2) Ammonia and trimethylamine for the renal failure, reported by the respective BioMed and Jacoby, M., Chemical & Engineering News (C&EN), Chicago 2004 for 2004 Pittcon.

(3) Acetone for diabetes, reported by the BioMed, and Chakrabory, S., et al., Current Science, Vol. 94, No. 2, January 2008;

(4) Nitric oxide for respiratory diseases including asthma and lung diseases, reported by the BioMed; Choi, J., et al., Biological Research For Nursing, Vol. 7, No. 4, 241-255 (2006) and Formanek, W., et al., Respiratory Journal, 2002, 19, 487-491;

(5) Ammonia for blood urea nitrogen, reported by Narasimhan, L. R., et al., PNAS, Apr. 10, 2001, Vol. 98, No. 8, 4617-4621;

(6) Pentane for the intestinal inflammation, reported by Kohoszka, J., et al., Diseases of the Colon & Rectum, Vol. 36, No. 6, 597-602, June 1993;

(7) Carbonyl sulfides for cystic fibrosis of lung diseases, reported by Vasich, T., UC Newsroom, UC, Oct. 17, 2005 for UC Irvine research results, and also published in the October 2005 online version of Proceedings of the National Academy of Sciences;

(8) Isoprene for cholesterol, reported by Jacoby, M., C&EN, Chicago 2004 for 2004 Pittcon; and (9) Hexane, methylpentane, o-toluidine and aniline for lung cancer, reported by O'Neil, H. J., et al., Clinical Chemistry, 1988, 34 1613.

Certain biochemical markers have been studied for their physiological basis. For example, acetaldehyde is for the ethanol metabolism, acetone for decarboxylation of acetoacetate, ammonia for protein metabolism, carbon monoxide for production catalyzed by heme oxygenase, carbonyl sulfide, carbon disulfide, ethanol, hydrogen and methane for gut bacteria, ethane for lipid peroxidation, hydrocarbons for lipid peroxidation/metabolism, isoprene for cholesterol biosynthesis, methanethiol for methionine metabolism, methanol for metabolism of fruit, methylamine for protein metabolism, nitric oxide for production catalyzed by nitric oxide synthesis, and pentane for lipid peroxidation (Risby, T. H., Solga, S. F., Appl. Phys. B, 85, 421-426, 2006).

In addition, a number of biochemical markers have been used in clinical tests, such as acetate for orocecal transit time, aminopyrene, caffeine, erythromycin, galactose, methacetin for liver function, glucose for insulin resistance, glycosyl ureides for orocecal transit time, ketoisocaproate and methionine for liver mitochondrial function, linoleic acid for fatty acid metabolism, phenylalanine for phenylalanine hydrolase activity, triolein for fat malabsorption, uracil for dihydropyrimidine dehydrogenase activity, and urea for H. Pylori infection (Risby, T. H., Solga, S. F., Appl. Phys. B, 85, 421-426, 2006).

It will be appreciated that the bio-markers also exist in patient urine, stool, serum, blood and saliva samples, so that the present invention including the dual sensor strategy also can be applied to test headspaces of these samples for medical diagnoses.

Breath samples have been recently used for diagnoses of the breast cancer (Alvarez, M., Fox News USA, reported on Feb. 28, 2008 for research at University of Michigan, and Dobson, R., Mail Online, at 2 Derry Street, London W85TT UK, reported on Jun. 5, 2008 for research conducted including at Imperial College in London).

Beside using them for medical diagnoses, the breath samples also can be used to monitor anaesthetic (propofol) of patients during surgery, since there have been found the propofol and two metabolites (2,6 di-isopropyl quinone and 2,6 di-isopropyl quinol) presented in the breath samples (Harrison, G. R., et al., British Journal of Anaesthesia, 2003, Vol. 91, No. 6, 797-799).

Human body odor is also of interest to study in the field of the medical diagnoses. For example, a typical skin odour of individuals is observed in the presence of schizophrenia (Smith, K., et al., Science, 1969, 166, 398). Recently, application of electronic nose instrument to study the skin odor includes detection of the schizophrenia (Di Natale, C., et al., Sensors and Actuators B, 2000, 65, 216). In addition, gaseous sample collection is also known long time ago (Gardiner, A. J., et al., Archives of Disease in Childhood, 1981, 56, 125-127). Therefore, the present invention also can study the body odor, through an in situ testing or testing the collected samples of the body odor, including those from foot, armpit and crotch areas, where bacteria are most likely to exist and grow to thereby cause the respective diseases.

In addition to correction of the humidity level as the background influence in application of the dual sensor arrangement, the present invention also can compensate other background influences such as the polymer film aging effect, and variations of the electrical properties caused by temperature variations.

Analytes will be influenced by temperature in the adsorption and desorption processes. In GC, a temperature programming including the gradient temperature programming is often applied for efficient separation of chemical mixture. Because of the small sizes of the respective single sensor and sensor compartment which result in low power consumption for temperature regulation on the sensor compartment including the sensor and analytes, the present invention can utilize temperature programming including the gradient and constant temperature programming to control adsorption and desorption processes on the analytes in the interaction with sensor electrodes. This is particularly benefit to the battery-powered and handheld electronic nose instrument of the present invention. Therefore, implementation of the temperature programming makes it possible that chemical characteristics of the analytes can be fully explored by the present invention method.

The present invention facilitates the design and development of the sensor instrument to have a small size, low cost and great portability. As an example, the present invention single sensor is well suitable for a disposable electrode configuration in the design of an electronic nose instrument.

EXAMPLES

The following are examples and experimental information of the present invention, regarding the single sensor operated by the electrical frequency sweeping technique as the core technique of the present invention, which are offered by way of illustration only and not by way of limitation and restriction.

A pair of electrodes were constructed with gold wires. The electrodes were 12 mm in length and had a gap approximately 1 mm. The electrodes through standard coaxial electrical cables were connected to an AC analyzing device, such as an "Agilent 4294A" impedance analyzer (Agilent, Palo Alto, Calif. USA). Calibration of electrodes was proceeded prior to sample measurement. A frequency sweeping method was used in impedance measurement, where resistance and reactance or impedance and phase angle were simultaneously obtained at each of various swept frequencies. The first experiment was conducted applying frequencies swept from 10 KHz to 500 KHz, and the second experiment used frequencies from 500 KHz to 1 MHz, wherein both experiments utilized two hundred and one swept frequencies.

Five chemicals as the analytes were used in impedance tests, including acetone, acetic acid, hexane, toluene, and water. In the first experiment, each chemical was alternatively measured six times. In doing so, each chemical was filled a half full into six vials, which were tightly sealed except for sample testing.

Before measuring each chemical sample, room air was first measured and recorded, and its impedance, resistance, and reactance were used as references. To measure a sample, a vial containing such sample was unsealed and placed where the liquid surface was close to the electrodes. A cotton ball was used to block a joint area of the electrode cables and vial opening to prevent variation of chemical vapor concentration inside the vial. Then a waiting period of ten seconds were applied before taking the electrical property data. After the measurement was done, the vial was immediately taken away from the electrodes and resealed. The measured vial was not reused.

The electrodes were then exposed to room air again for about ten minutes before the next measurement. The sequence of measuring chemicals was in the order of toluene, acetone, hexane, water, and acetic acid. The second and subsequent (up to the sixth) measurements were taken with the same sequence. Change of an electrical property is obtained from the following equation, which is the contribution of the respective tested chemicals:

$$\text{Change of electrical property} = \text{Electrical property of sample} - \text{Electrical property of air} \quad [7]$$

Thus a raw data matrix was constructed from collecting electrical properties of the respective chemicals at various frequencies, which were randomly selected from the swept frequencies. Each two adjacent columns of the matrix represented resistance change and reactance change at one frequency, respectively, and each row represented a single measurement of a chemical. Analysis of the data in the matrix was conducted by application of a software having a PCA algorithm, which was installed in a personal computer.

Figure 1:
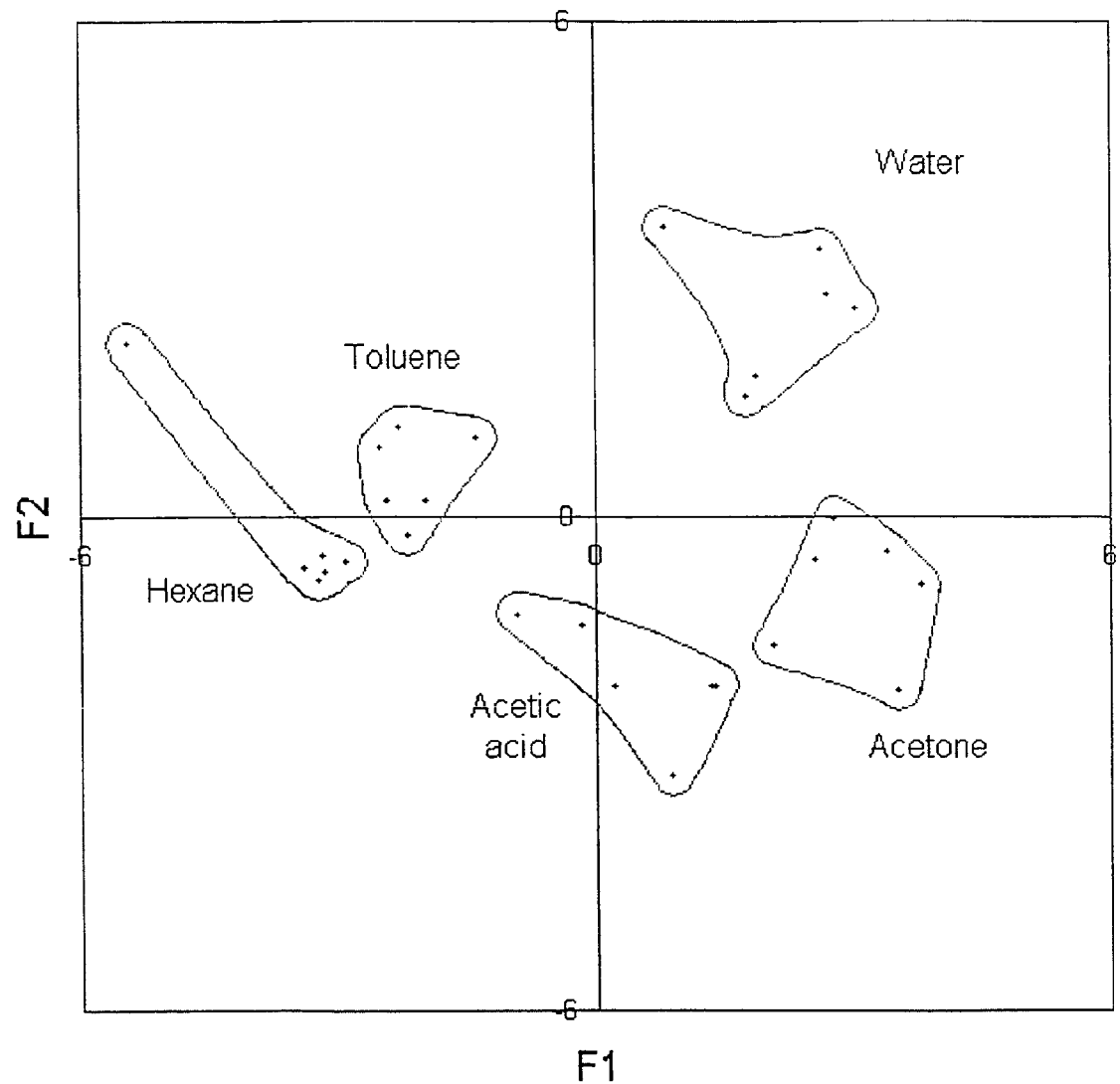
FIG. 1 is an illustrative plot diagram showing the result of classification for five (5) chemicals from a principal component analysis, where resistance and reactance at each of seven (7) frequencies are used in the analysis, wherein the frequencies are randomly selected from two hundred and one (201) swept frequencies ranging from 10 KHz to 500 Khz.

Referring to FIG. 1, there is shown the principal component analysis (PCA) for chemicals of acetic acid, acetone, hexane, toluene, and water with the respective resistance and reactance data obtained at the frequencies as 10, 20, 50, 100, 200, 300 and 500 KHz, which were randomly selected from the swept frequencies. As illustrated, the electrical information of the chemicals is simplified after applying the principal component analysis and presented in accordance with two principal components F1 and F2. During data analysis applying PCA, the raw data of change of resistance and reactance in the matrix was normalized to the length one before further processing.

It is clear from the graph of FIG. 1 that the test results from the same chemical are grouped in a particular area, as the five chemicals are separated and located in different areas of the F1 and F2 plane. In other words, with the aid of the PCA, a pattern of distributing five chemicals was recognized in the first and second principal component plane. The results of the first and second principal component plotting indicate that chemicals can be distinguished with their respective electrical properties, such as impedance and its phase sensitive components (i.e., resistance and reactance) obtained at each of the swept frequencies ranging from 10 KHz to 500 KHz.

Figure 2:
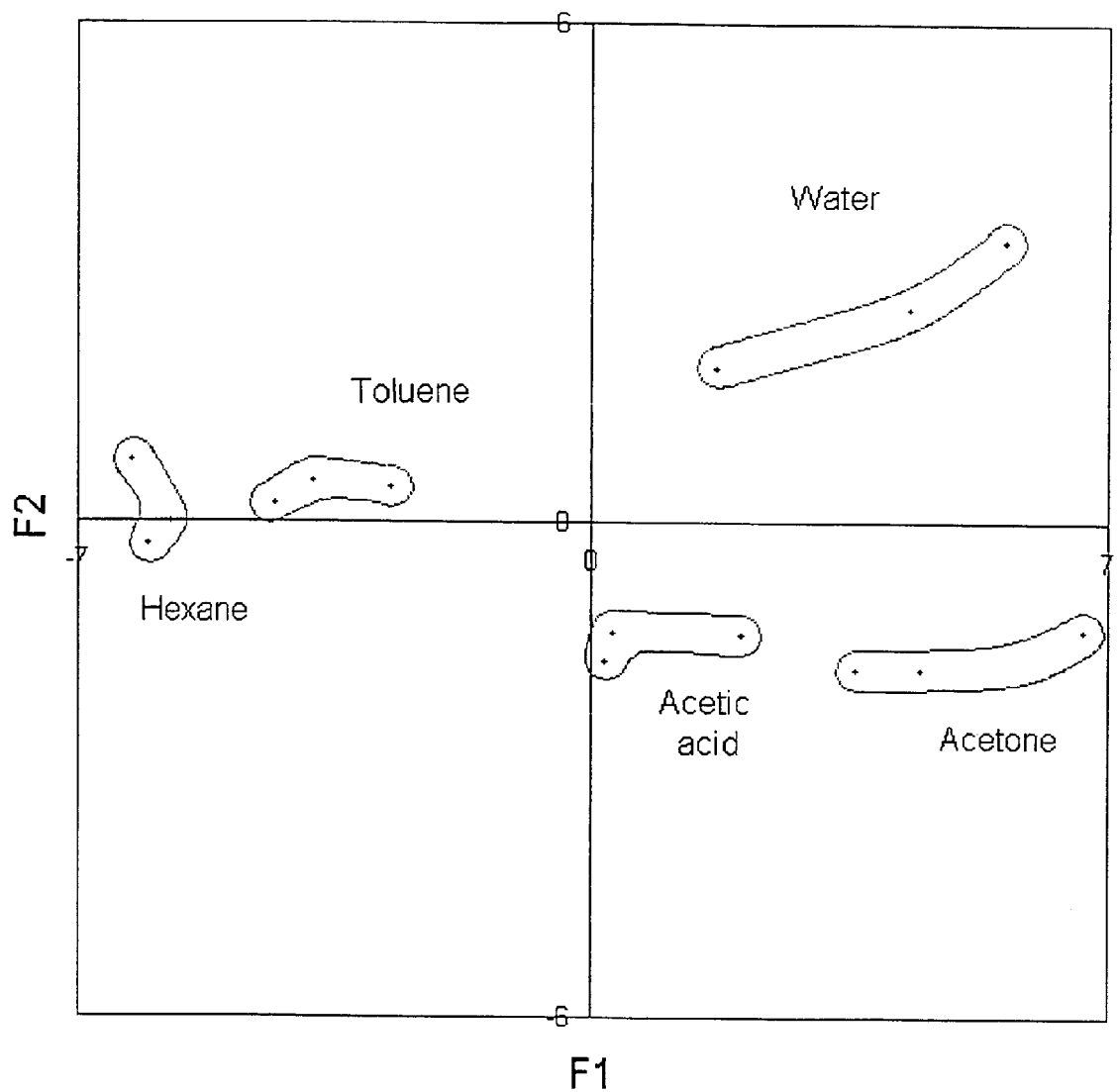
FIG. 2 is an illustrative plot diagram showing the result of classification for five (5) chemicals from the principal component analysis, where resistance and reactance at each of eleven (11) frequencies are used in the analysis, wherein the frequencies are randomly selected from two hundred and one (201) swept frequencies ranging from 500 KHz to 1000 KHz.

Referring to FIG. 2, there is shown the results of separation from the principal component analysis for the same chemicals of acetic acid, acetone, hexane, toluene, and water, where their resistance and reactance data were obtained at the randomly selected frequencies 502, 550, 600, 651, 700, 750, 801, 850, 901, 949 and 1,000 KHz among the swept frequencies. In the second experiment, each chemical was repeatedly measured three times in accordance with the procedure described above. During data analysis applying the PCA, the raw data matrix of change of resistance and reactance was normalized to the length one before further processing. The results indicate that impedance and its components can be used to identify chemicals, according to a pattern of the respective five chemicals that are distinguishably distributed in the first and second principal component plane.

A third experiment was conducted to test three analytes of acetone, toluene and a liqueur containing approximately 44% alcohol that is belong to a chemical mixture. The experimental conditions were generally the same as those illustrated above, except for: (1) The electrodes were 13 mm in length and had a gap approximately 0.5 mm, which were made of wire leads cut from commercial resistors. The leads were copper wires coated with tin metal film; (2) each analyte was stored in one vial that was reused in the experiment; (3) five measurements were conducted for each analyte, and (4) resistance and reactance at seven frequencies of 10, 20, 50, 100, 200, 300 and 500 KHz were used for data analysis, wherein the frequencies were randomly selected among two hundred and one frequencies swept from 10K to 500 KHz.

Figure 13:
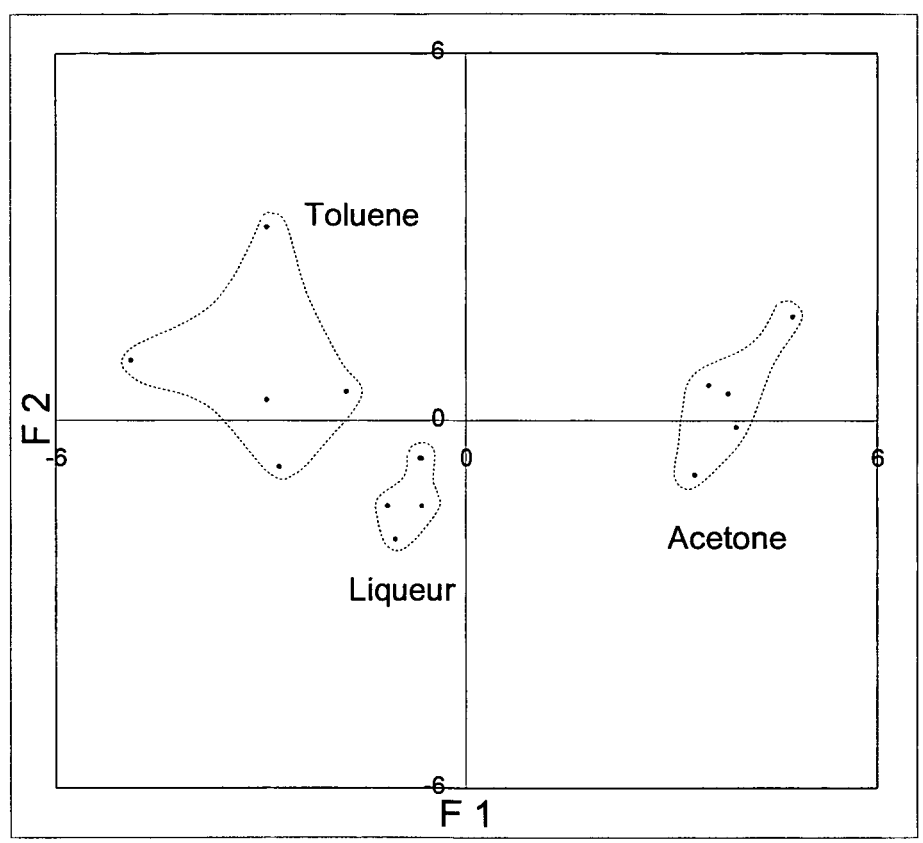
FIG. 13 is an illustrative plot diagram showing the result of classification for three (3) analytes from a principal component analysis, where resistance and reactance at each of seven (7) frequencies are used in the analysis, wherein the frequencies are randomly selected from two hundred and one (201) swept frequencies ranging from 10 KHz to 500 KHz.

Referring to FIG. 13, results of the third experiment indicate that impedance and its components can be used to identify chemicals, according to a pattern of the respective three analytes that are distinguishably distributed in the first and second principal component plane. It will be appreciated that the liqueur is an analyte being a chemical mixture of water, alcohol having ethanol as the main ingredient, and various other volatile hydrocarbons. Therefor, the headspace of the liqueur also contains those mixed chemicals. This experiment demonstrates that electrical properties can be used to distinguish analyte of the chemical mixture, as compared with other analytes that are the respective different chemicals.

It is will be appreciated that the application of the above specified frequencies is only for illustration of effectiveness according to the principle and scope of the present invention. It is not intended here to restrict other frequencies, which are different from the swept frequencies that have been disclosed above in application of the present invention.

It will be further appreciated, following known validation procedures of the PCA that are discussed elsewhere, a model can be established for a defined experiment such as the first experiment discussed above that has the defined experimental procedures and the data analysis procedures including the data presentation procedure. Therefore, following the known experimental and validation procedures a data base can be established, which includes a plurality of raw data and models for the respective various known analytes. After establishing the database, an unknown analyte can be predicted by comparing the PCA results of the unknown with the models of the respective, known analytes in the database, wherein the comparison can be conducted with the known procedures, including visualization that is one of characteristics of the principal component analysis.

It will be additionally appreciated that, the present invention is not limited to only apply the PCA pattern recognition analysis and validation of the AC electrical properties of the respective analytes in fluids for establishing models to thereby predict unknowns. The present invention can apply any of the existing known analysis algorithms comprising multivariate analysis algorithms including the pattern recognition algorithms to classify and identify analytes in fluids, since those of ordinary skill in the art, who can compare strength with weakness of each algorithm, can choose one algorithm that is best for the particular interest of study. The additional analysis algorithms are known elsewhere (Beebe, K. R.; Pell, R. J.; Seasholtz, M. B.; Chemometrics: A Practical Guide, Wiley, N.Y. 1998; J. of Chemometrics, John Wiley & Son, Ltd.), comprising SIMCA (Soft Independent Modeling of Class Analogy), KNN (K Nearest Neighbor), HCA (Hierarchical Cluster Analysis), CDA (Canonical Discriminant Analysis), CLS (Classical Least Squares), PCR (Principal Component Regression), PLS (Partial Least Squares Regression), supervised and unsupervised learning neural network and fuzzy neural network techniques.

Furthermore, it can be understood from the above experimental results that, instead of identifying analytes in fluids from application of the swept frequency detection, the present invention can also be used to detect the presence of analytes of interest with a single frequency detection. For example, in GC analysis, mixed chemicals of an analyte are eluted separately out of the column by a carrier gas (usually hydrogen, or helium, or nitrogen). Each chemical can be detected in presence because of different AC electrical properties from the carrier gas and chemicals at the applied frequency, such as the impedance. The above illustrated chemical separation process is also occurred in LC, wherein a solvent or a solvent mixture carries out each chemical in an analyte of the chemical mixture. Therefore, the chemicals can be detected by applying one of the above disclosed electrical properties at a frequency.

In the application of the present invention from a preferred embodiment to design a GC detector, the first spatial electrode of the single sensor 1 is a collar shaped hollow cylinder. The hollow cylindrical electrode is positioned at a top of a hollow jet connected to the end of the column, wherein the jet and hollow electrode are further positioned coaxially to the column end. The second spatial electrode of the single sensor 1 is a straight and thin member, which is positioned so as to be aligned with a rotation axis of the hollow cylindrical first electrode, either inside or outside of the cylindrical electrode. The GC detector from the present invention has a number of advantages, as compared with the existing GC detectors including the flame ionization detector (FID), thermal conductivity detector (TCD) and electron capture detector (ECD). The advantages include non-destructive, universal, simple for easy manufacturing and low cost.

Furthermore, for the above disclosed GC application of detecting presence of the chemicals using the impedance or current or voltage, the periodic electrical excitation signals of voltage or current can be applied to the GC detector of the present invention, which include the square, triangular and sawtooth wave forms. This will simplify electrical circuits of the analyzing device.

As another example, detection of known flammable gases such as methane is critical for safe operation in the mine industry. Detection of such gases can also be achieved by using the single sensor operated at a frequency by the excitation signals including the square, triangular and sawtooth wave forms to detect one electrical property.

In addition, referring to FIGS. 7A and 7B there is illustrated a single sensor according to the present invention, wherein the two electrodes may be formed in many ways. For example, when a first electrode is positioned at a location close to a sidewall of a container or other structure made of electrically conductive material which is electrically grounded, then the sidewall of the container or other structure may serve as a second electrode. The analyte in the fluid to be tested can be directed to pass through the gap between the first electrode and the sidewall of the container or other structure, which functions as the second electrode.

The present invention single sensor operated by the periodic including AC electrical excitation signals with swept frequencies has many advantages. It utilizes a single analytical sensor from one measurement to generate spectra of the patterned electrical properties to record the analyte characteristics. The small size of the sensor which results in low power consumption on sensor temperature regulation and small volume requirement also allows the practical implementation of the dual sensor strategy which, in addition to the analytical sensor, incorporates a reference sensor with the identical configurations. With this dual sensor strategy, effects of background subjects can also be eliminated including humidity levels, aging effect of the polymer films and changes in testing including sensor responses induced by temperature variations.

The single sensor and method of the present invention also operate using swept frequencies including a preferred low frequency range between 10 KHz and 1 MHZ. Application of the swept frequencies enables the application of the single sensor having a small size to obtain the analyte patterned electrical information. The small sensor including a small sensor compartment determines a low power consumption to control temperature of the sensor compartment containing an analyte in a fluid, which is positioned between the sensor electrodes. It further allows the use of the temperature programming including the gradient and constant temperature programming to improve the detection and identification of the analyte in the fluid. In addition, applying the electric periodic excitation including the AC electrical excitation signals, the present invention provides the capability to use all types of adsorbent, absorbent and sorbent materials, including organic, inorganic, and metal materials. Combined with all of the above discussed advantages, it results in the present invention sensor instrument that is low in cost to produce, compact in size, portable, and easy to use.

The above disclosure introduces the core technology of the present invention having a single sensor operated by the periodic including the AC electrical excitation signals having swept frequencies. The following disclosure will introduce the sensor instrument system of the present invention.

The sensor instrument system is comprised of a portable stand alone sensor instrument, and a central station, which are remote from each other. The sensor instrument has capabilities, comprising detecting and identifying analytes in fluids, locating the analyte geographic positions and wirelessly transmitting and receiving data. The central station connects to a data receiving site through connecting to a network means. The data receiving site is comprised of means for wirelessly communicating with the sensor instrument for transmitting and receiving data. Therefore, the system comprises the ability of wirelessly communicating data and locating geographic positions of the respective analytes. In this setting, it will provide maximum mobility in remote detection and identification of analytes in fluids, and incorporating with geographic positions of the respective analytes. Furthermore, a mapping of the analytes in a region can be in situ constructed if applying a plurality of the identical sensor instruments, which are movably positioned at the respective local areas of the region.

The sensor instrument is configured after combining the core technology of the present invention with the existing technologies in both hardwares and softwares of wirelessly transmitting data and obtaining data of the geographic positions from application of the GPS.

It will be appreciated that the structural configuration of an analytical instrument with a microcomputer built in has been well known. One can be found in "Chemical Instrumentation: A Systematic Approach, Third Edition", Chapters 5 and 6, Strobel, H. A., Heineman, W. R., John Wiley & Sons, Inc. 1989. In general, the analytical instrument is comprised of an analog section (as an analytical detector) connected to an interface including an analog-to-digital converter (ADC), which is further connected to a digital section that has a built-in microcomputer. Specifically, the analytical detector through the interface is connected to an input/output bus of the microcomputer.

In addition to the structure configuration of the analytical instrument with the built-in microcomputer, the necessary components for designing the instrument having the built-in microcomputer include ADC, logic circuits, multiplexer, filters, amplifiers, address, central processing unit (CPU) including arithmetic-logic unit (ALU) and register as part of the CPU, memory bus, byte, digital-to-analog converter (DAC), direct memory access (DMC), IEEE-488, input/output (I/O) port, peripheral including an inputting device such as a keyboard or a touch-screen inputting mechanism, random access memory (RAM), read only memory (ROM), counter, integrated circuits, RS-232, digital data acquisition module, word, instructions, data, programs, operating system, low and high level languages, application softwares, and display. Therefore, all above known components are incorporated herein for simplifying this disclosure.

Referring to FIGS. 1, 2 and 13, there are illustrated results of the detection and identification of the analytes in the fluid. The results were obtained after application of the alternating current analyzing device such as the Agilent 4294A impedance analyzer connected to the single sensor, and the application software having the PCA algorithm that was installed in the personal computer for the electrical data analysis. It will be appreciated that if using one of the RS-232 and IEEE-488 procedures connects the Agilent 4294A to the personal computer installed with appropriate hardware and software including a driver for connection, an instrument assembly can be established. The assembly serves as a basis for the present invention sensor instrument, wherein the AC analyzing device acts as the analytical detector of the instrument assembly for measuring samples of analytes in fluids.

As illustrated in the Nagle Publication, there is disclosed a general configuration of an electronic nose instrument, comprising three components that operate serially on an odorant sample: a sample handler, an array of gas sensors and a signal-processing system.

Figure 8:
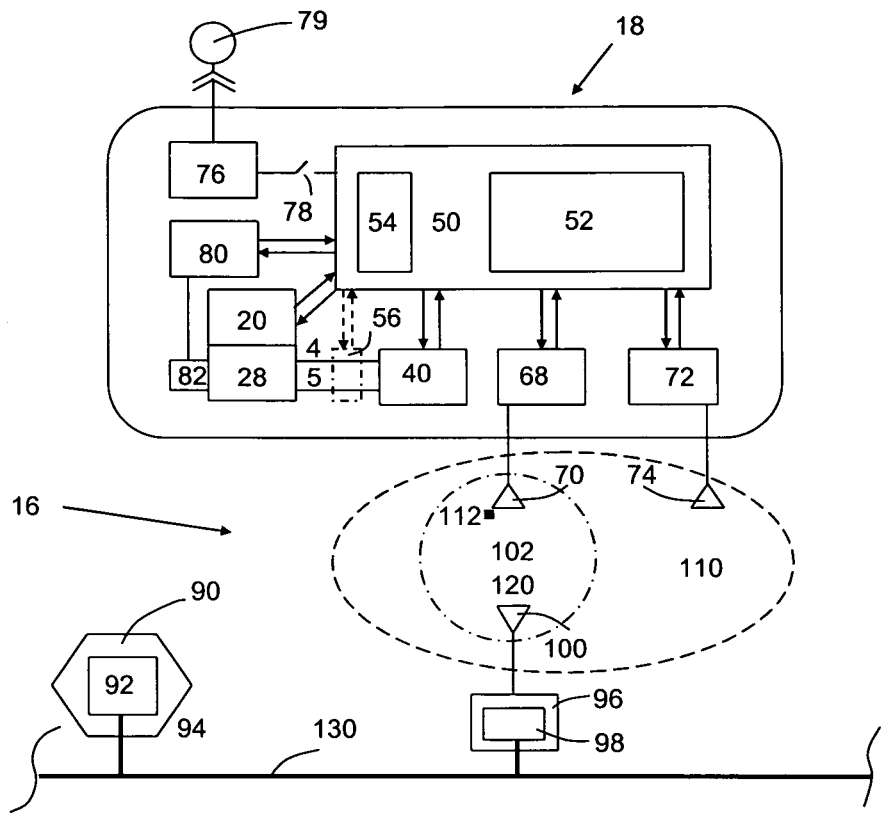
FIG. 8 shows a schematic block diagram of the structural configuration of the present invention sensor instrument system including a sensor instrument and central station through a network means connected to a local receiving site. The figure also illustrates that the sensor instrument wirelessly transmits data to the remote central station including a geographic position data of the instrument, which is obtained after its interacting to the GPS environment.
Figure 9:
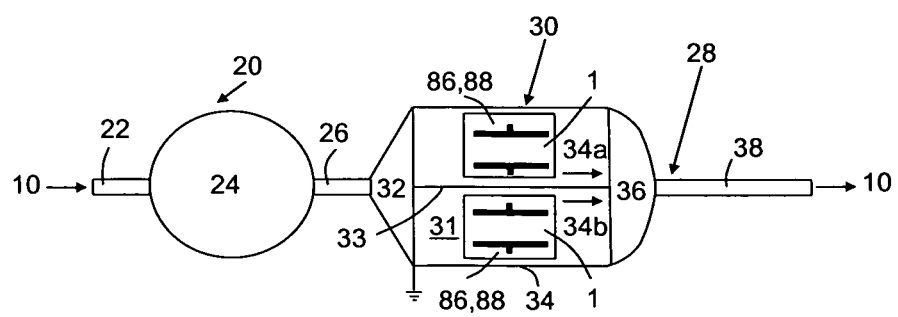
FIG. 9 shows a schematic diagram in a top view of the sample handling module linked to the sensor compartment module, wherein a top of a middle section of the sensor compartment is removed so that two sensors are seen that are positioned in the respective two subchambers.

Therefore, referring to FIGS. 8 and 9, the sensor instrument system 16 of the present invention is comprised of an integrated sensor instrument 18, and the central station 90 including a central computer and server computer 92 connected to a local receiving site 96 through connection to a network means 130. The integrated sensor instrument 18 is configured to comprise eight connected modules, including a sample handling module 20 having a sample driving unit 24, a sensor compartment module 28 attached to an exterior heater 82 of a heating module 80, a detection module 40, a microcomputer module 50, a data transmission module 68, a GPS receiver module 72, and a power module 76.

The microcomputer module 50 including a built-in display 52 and a set of buttons 54 functions as a miniaturized personal computer. The key function of the microcomputer module includes digitized signal processing to identify analytes, and instructions for operation of the rest modules in the sensor instrument. For example, through applying a signal pre-processing algorithm, the difference as disclosed in Equations [5-7] of the electrical properties of the respective analytes can be obtained at each frequency. Therefore, a matrix of the raw data set can be constructed for the further data analysis of the analyte identification. It will be appreciated that, in addition to this difference, other algorithms reported elsewhere also can be applied for the signal pre-processing. In addition, the module 50 can also serve as a digital data acquisition section for the rest modules in the sensor instrument 18.

The module 50 is comprised of necessary components for self operation including a CPU, memory bus, memory including data, instruction and addresses, and input/output bus. The module 50 also includes a computer operating system. In a preferred embodiment, it is a commercial window based computer operating system.

The module 50 is installed with a sensing operation software. The module 50 is also installed with the application software of analysis algorithms comprising pattern recognition algorithms including the PCA algorithm, and a software to encrypt the data when a secure data transmission is required and another software of the GPS positioning maps. Since the module 50 is comprised of the buttons 54 functioning as the inputting device, a user of the sensor instrument can select the desired sensor instrument functions by pressing the buttons to complete inputting parameters or instructions for operating the instrument, for example, to launch the sensing operation software. Instead of having the physical buttons, the display screen 52 has a function of inputting instructions of operation. Therefore, the user can input instructions by pressing appropriate areas of the display screen 52. In addition, the module 50 can display the obtained electrical data in a real-time fashion according to the elapsed times or the swept frequencies. The module 50 is also comprised of the USB or RS-232 or IEEE 488 port of an electrical wire connection for possible applications including data transfer.

In a preferred embodiment, the sensing operation software is a window based software. It comprises programs used to direct the operation of the sensor instrument 18 including testing analytes, collecting data, storing data and linking the disclosed application softwares. For example, it comprises instructions to operate the sample handling module 20 and detection module 40 for testing analytes in fluids, instructions for collecting data of analysis, instructions to operate the GPS receiver module 72 for collecting data of the geographic positions, and instructions to operate the data transmission module 68 for wirelessly transmitting data. The software comprises the following basic sections.

A first registration section is for recording identities of analytes, including the analyte names and types. If an analyte is a patient biological sample, the identities include encrypted patient name, sex, ethnicity and age. If an analyte is not related to the patient biological sample, an exact sample type will be input. The testing date and time will be automatically recorded from the built-in clock for authenticity.

A second section is for inputting AC testing parameters, comprising a magnitude of the excitation signals, and types of frequency modes including a specific frequency for a single frequency mode and a sweeping frequency mode having starting and stopping frequencies. In the frequency sweeping mode, it further includes options for collecting electrical properties according to a number of all swept frequencies, or specific number of randomly selected frequencies, or a total number of exact frequencies within the swept frequencies. The second section also includes options of "yes" or "no" to operate the GPS receiver module, and parameters to operate the sample driving unit 24 of the sample handling module 20.

A third section is for selecting options to process data of the detected electrical information, whether or not it is processed by the sensor instrument or by the central station when measurement is completed. This refers to two embodiments on data that is transmitted by the sensor instrument 18.

One embodiment will transmit the data to a local receiving site, comprising detected and identified analytes and the geographic positions shown where the respective analytes under test are positioned. In this configuration, referring to FIG. 8, the results of the analyte that is analyzed locally are transmitted to a local receiving site 96 and then transferred to the remote central station 90. The station is comprised of the central computer including the server computer 92 functioning including data storage, wherein the same software of the GPS positioning maps is also installed. Therefore, the results of the analysis and the geographic positioning data can be stored and displayed in the central computer 92.

In another embodiment, the obtained electrical properties of the respective analytes in fluids according to the swept frequencies and the analyte geographic positions can be wirelessly transmitted to the central computer 92 of the central station 90. It will be appreciated that, the central computer is also installed with the same application softwares of the respective GPS positioning maps and analysis algorithms including the PCA algorithm. Therefore, the data of the analyte electrical properties can be processed at the central station, so that results of the respective detected and identified analytes can be stored and displayed along with the respective geographic positions.

If the embodiment of locally processing data is chosen, the sensing operation software will automatically launch the application software of the analysis algorithms including the pattern recognition algorithms for identification of analytes after measurement of the analytes in the area is completed.

A fourth section is for choosing options how to send detected including analyzed information, wherein the options include automatically sending when the corresponding process is completed, or sending after receiving a manually input instruction.

The sensing operation software will be activated after pressing an icon "run" that is positioned at the end of the software, which also activates operation of the sensor instrument 18.

It will be appreciated that, the above disclosed sections of the sensing operation software only includes very basic parameters and instructions for a run. A list of the comprehensive parameters and instructions is readily available to those of ordinary skill in the art with reference to the disclosure of the present invention and various existing instrument operation softwares including one in the GC instrument.

Referring to FIG. 9, there is illustrated that the sample handing module 20 is mechanically linked to a hollow sensor compartment 30 of the sensor compartment module 28.

The sample handling module 20 functions to collect and then transfer samples of analytes in fluids, comprising the middle sample driving unit 24, which is simultaneously linked to the respective inlet 22 and outlet 26. In a preferred embodiment, the middle sample driving unit 24 is a mini- or micro-pump, which is powered by an electrical force. However, it also can be powered by a mechanical force or human force. The inlet and outlet 22 and 26 can be in a form of a hollow pipe or one of channels or any other means having interior passages for regulating flow of analytes in fluids. In a preferred embodiment, the inlet and outlet 22 and 26 are made of soft pipes. However, the inlet, pump and outlet 22, 24 and 26 should not strongly adsorb analytes in fluids, when they pass through interior of the sample handling module 20.

The outlet 26 of the sample handling module 20 is mechanically linked to a front section 32 of the hollow sensor compartment 30 of the sensor compartment module 28. The sensor compartment 30 is made of metal materials such as copper or metal alloy materials for shielding electromagnetic radiation, when the compartment is electrically grounded. The hollow sensor compartment 30 having a limit thickness is comprised of the front section 32 connected to a middle section 34, which is further connected to a rear section 36 that links an exhaust means 38, such as an exhaust pipe. In this setting, a sample 10 of an analyte in a fluid in the exterior environment adjacent the sample handling module 20 will be driven by the pump 24 to enter into the inlet 22, flow through the pump 24 and outlet 26 to enter into the sensor compartment 30, and then finally exist from the exhaust means 38.

The front section 32 of the sensor compartment has a shape of an isosceles triangle. As illustrated, a front tip of the section 32 is linked to the outlet 26, and a rear wide transverse closed side of the section 32 is connected to a front side of the middle rectangular section 34 of the sensor compartment 30. It will be appreciated that, when it enters into the front section 32, the sample 10 will reduce a flow speed due to a wide transverse width of the front section 32, as compared with a narrow interior size of the outlet 26. In this situation in addition to the limited thickness of the sensor compartment 30, a laminar flow can be achieved when the sample flows through the sensor compartment 30. The arcuate or round rear section 36 of the sensor compartment 30 will reduce formation of the sample turbulent flow, which also contributes to achieve the laminar flow of the sample. It will be appreciated that the laminar flow creates a uniform distribution of the sample to the sensor electrodes.

Referring to FIGS. 9 and 10 again, the interior of the middle section 34 of the sensor compartment 32 is divided by a middle upward wall 33 positioned in parallel with the flow direction, which forms first and second identical subchambers 34a and 34b. Within each sub-chamber, there is positioned one identical single sensor 1 having two electrodes, aligned with the flow direction. However, it will be appreciated that each identical sensor 1 having two electrode can also be positioned at any angle to the flow direction including the angle of 90 degrees. Referring to FIG. 8, it will be appreciated that, lines 4 and 5 represent connection of the respective two identical sensors 1 to the detection module 40.

As illustrated in an early section of this disclosure, two electrodes of the single sensor 1 can be positioned in space to be spatial electrodes, or positioned onto the respective ceramic and silicon substrates 86 and 88 to be the respective thick and thin film electrodes. Referring to FIGS. 9 and 10, in the case when the sensor 1 has either thick or thin film electrodes, the respective ceramic substrate 86 or silicon substrate 88 is adhered to the interior side 31 of the bottom side 34c of the middle section 34 of the sensor compartment 30. It will be appreciated that both ceramic, silicon and metal materials are good heat conductors. Therefore, if an exterior heater 82 of the heating module 80 is attached to the exterior side of the sensor compartment 30, wherein heating of the heater 82 is controlled by electronics of the heating module 80 according to the temperature programming, it can easily control the temperature of the sensor compartment module 28, including the inside positioned each sensor 1 having various types of electrodes contacted by the sample 10 of the analyte in the fluid. This is because of the small size of the each sensor 1 that only requires a small volume of the subchamber of the sensor compartment 30, which further results in a low power consumption for the temperature control.

As illustrated above, the metallic sensor compartment 30 when it is electrically grounded shields the electromagnetic radiation emitted by the first sensor 1 which is applied by the AC electrical swept frequencies. Similarly, electromagnetic radiation emitted by the second sensor 1 is also shielded. Therefore, application of the sensor compartment can prevent influence from a possible cross talk of the electromagnetic radiation emitted by the first and second sensors 1.

It will be appreciated that, by providing an example of two sensors connected to the detection module, the above illustration discloses one embodiment of the present invention, which employs at least two sensors to detect and identify analytes in fluids. Implementation of the embodiment follows the spirit and scope of the present invention, finding dimensions that describe characteristics of the analytes in the fluids.

In this embodiment, referring to FIG. 6, adsorbent materials 8 are positioned between the paired electrodes of one of the at least two sensors. During testing analytes in fluids, each analyte in a fluid is tested by each of the at least two sensors according to a testing procedure. The sensor filled with the adsorbent materials will record the AC related electrical properties including resistance and reactance as the detectable information for an adsorbed chemical or adsorbed chemicals from the analyte in the fluid, when the adsorption process is completed.

Obviously, in a situation if each of the analytes is a chemical mixture, dimensions of the respective resistance and reactance from the sensor electrodes filled with the adsorbent materials reflect the characteristics of adsorbed chemical or chemicals that are a part of the chemical mixture. They are different from dimensions of the resistance and reactance from the sensor electrodes without filled with adsorbent materials, which reflect an overall characteristics of all different chemicals in the analyte. In another situation if each of the analytes is a different chemical, the resulting electrical properties from the sensor electrodes filled with adsorbent materials will have a high signal-to-noise ratio for each analyte, as compared with those from the sensor electrodes not filled with adsorbent materials. The high signal-to-nose ratio is still positive for the analyte detection and identification. Therefore, having the spirit and scope of finding characteristic dimensions of analytes in measurement, the present invention can conduct better detection and identification of analytes in fluids with implementation of a strategy having the at least two sensors when it is needed.

Following the above analogy, another embodiment of the present invention is that each of the at least two sensors is filled with different adsorbent materials between the respective paired electrodes.

It will be further appreciated that, continuing to follow the spirit and scope of increasing dimensions to describe analytes in fluids, a sensor configuration of the present invention can utilize one or more of the existing sensors disclosed in the Nagle Publication and the 333 Lewis Patent to be one or more sensors in the configuration, and the remaining sensors can be the sensors of the present invention for completing this configuration. This is because the existing sensor technologies detect measurable information about the respective analytes in the different dimensions, as compared with the sensors having the core technology of the present invention.

Figure 11:
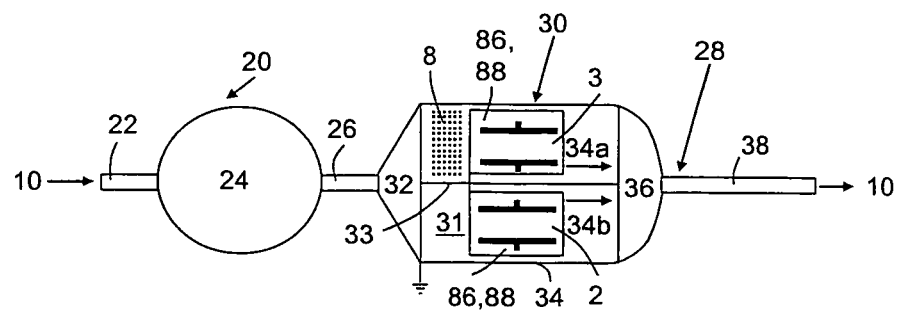
FIG. 11 shows the same structural configuration of the sensor compartment module in FIG. 9, in addition to show that adsorbent materials 8 are positioned at the front of one of the subchambers to adsorb the analyte in fluid, so that only the fluid can pass between the sensor electrodes positioned inside of the subchamber.

Referring to FIG. 11, there is illustrated another embodiment for applying the dual sensor strategy, wherein one sensor, positioned in the subchamber 34b serves as the analytical sensor 2, and another one positioned in the subchamber 34a serves as the reference sensor 3. They can be in the forms of spatial, thick film and thin film electrodes filled with or without the adsorbent materials 8. However, the same adsorbent materials 8 are positioned at the front of the subchamber 34a for trapping chemical or chemicals of interest, so that only those that are not interest for the study, which can pass through the adsorbent materials 8, can continually pass between two electrodes of the reference sensor 3.

As disclosed before, after combining the electrical properties of the respective analytical and reference sensors 2 and 3, there remains only electrical properties of the chemical or chemicals of the interest including those which serve as the biochemical marker or markers. This is an effective way to detect known chemical or chemicals including biochemical marker or markers of an analyte for the analyte identification including the medical diagnoses of types of diseases.

In addition to the embodiment of the integrated dual sensor 13 shown in FIG. 11, the analytical and reference sensors 2 and 3 have the respective independent sample handling modules if they are in the separated form.

As disclosed before, because of its small size, simple structure and low cost, the single sensor of the present invention is practically suitable for the disposable electrode configuration. In design of the disposable electrodes, for example, which are positioned inside of the respective sensor subchambers 34a and 34b, the front section 32 of the sensor compartment 30 can be designed to be detachable. This means that the front section 32 can be press-fit to connect to the middle section 34 of the sensor compartment 30. The disposable electrodes including the spatial, thick and thin film electrodes of the sensor also can be in the same press-fit manner to contact the respective metal sockets covered with appropriate electrical insulation materials, wherein the sockets that are positioned inside of the respective subchambers 34a and 34b connect to the detection module 40. Following this concept, a detailed design is obvious for those of ordinary skill in the art, therefore the present invention can have the disposable single sensors, which is one unique feature of the present invention.

The detection module 40, functioning as the AC analyzing device 9, comprises a component of electronic circuits to generate AC excitation signals having swept frequencies, which can be applied to the single sensor containing a sample of an analyte in a fluid to obtain the sample electrical properties, wherein the properties can be measured by another component having electronic circuits of the detection module.

The detection module 40 can be manufactured according to a number of electronic structures that are well known. It can be configured following the electronic configuration of the Agilent 4294A comprising a digital control, source, transducer, and vector ratio detector, wherein the source provides all analog signals of the AC excitation voltage having swept frequencies and variable voltage magnitudes that are applied to the sample, the transducer comprises a transform of the measured sample impedance into two AC signal voltages, the vector ratio detector comprises conversion of two AC voltages into digital data, and the digital control comprises digital data processing for outputting results of the sample measurement.

The module 40 can also be designed from electronic circuits based on the analog Lock-in principle, interfaced by including ADC, which is further connected to the digital section for data acquisition (Princeton Applied Research, Oak Ridge, Tenn. USA). In addition, the digital analogy of the Lock-in principle, which is the digital correlation, can be additionally applied (Solartron, Farboroagh, Hampshire UK).

It will be appreciated that the above disclosed techniques apply AC signals with swept frequencies comprising a sinusoidal wave that sequentially varies frequencies to excite an analyte as a measurement time elapses, wherein there is only one frequency at any point of time when the analyte is excited. Instead of such one-frequency excitation mechanism, a polyfrequency excitation mechanism is also appropriate to construct the detection module 40 (Zahner-Elektrik Gmbh & CokG, Kronach Germany), which applies a plurality of sinusoidal waves having the respective different frequencies to excite an analyte at any point of time. Such excitation could further employ the Fourier transform techniques.

Therefore, the detection module 40 can be configured comprising a detector section from selecting one of those known detection mechanisms, connected to an appropriate interface such as ADC that further connects to a digital acquisition section containing a main CPU. Within the sensor instrument 18, the detection module 40, which is connected to the single sensor 1, connects to the microcomputer module 50. The advantage of the detector module 40 having the self contained digital acquisition section including the memory and CPU is for fast data analysis. This is due to the fact that the detection module 40 additionally undertakes a task of processing the detectable information including converting the information in analog form into digital form for identifying analytes, which is one of the tasks of the microcomputer module 50, as disclosed previously.

According to this configuration, the CPU of the microcomputer module 50 can mainly instruct operation of all other modules in the sensor instrument. Therefore, a better performance of the sensor instrument can be achieved including the fast data analysis.

As an alternative, the detection module 40, which can share function of the digital acquisition of the microcomputer module 50, only comprises the analog circuits as the detector according to one of the specific mechanisms, which is then interfaced by including the ADC.

As disclosed before, if it is only for one frequency detection, the periodic excitation signal is adequate for the detector module, comprising the square, triangular and sawtooth wave forms.

Referring to FIG. 8, the data transmission module 68 is comprised of an antenna or antenna means 70 connected to a transceiver that connects to a digital module having a simple CPU, which is connected to the microcomputer module 50, so that the module can transmit through the antenna means 70 digital data of the analyte information and geographic position that is encoded in a high frequency signal of the electromagnetical waves. In this configuration, a two-way communication can be established. This means, referring to FIG. 8, the sensor instrument 18, which is movably positioned at a local area 102, not only can send the data but also can receive instruction of the central station 90 positioned at a remote area 94. This communication is available through incorporation with the local receiving site 96 under a communication environment 120 that is an electromagnetic field generated by the high frequency signal of the electromagnetic radiation (waves) transmitted from the data transmission module 68 (or the receiving site 96), wherein the site 96 (or the module 68) receives the signal. In addition, the site 96, which connects to the network means 130, is connected to the central station 90, and is positioned at the same local area 102 as compared with the positioned instrument 18.

As illustrated in FIG. 8, the GPS receiver module 72 is comprised of an antenna or antenna means 74 connected to a main GPS receiver and other necessary digital circuits including a CPU and additional clock to connect to the microcomputer module 50. The module 72 receives a geographic position 112 of an analyte in a fluid (or the sensor instrument 18) from interacting to the GPS environment 110 comprising a plurality of satellites. Therefore, the position 112 that is detected for the location of the instrument 18 can be further displayed on the computer display 52 since the GPS application software is installed in the microcomputer module 50. Alternatively the position 112 can be transmitted through the module 68 to the central computer 92 of the station 90, and then displayed on a screen of the central computer.

The heating module 80 that includes the exterior heater 82 and circuits including a digital section can be constructed applying circuits and heater, which are available elsewhere, wherein the digital section of the circuits is connected to the microcomputer module 50.

The power module 76 is comprised of a physical switch 78, DC rechargeable batteries providing power to modules of the sensor instrument 18, electronic circuits for converting local AC city power 79 into the DC voltage for charging the batteries, and other circuits that control the supply of the DC power to other modules including the sample handling module 20 and heating module 80 under the instructions of the microcomputer module 50. For example it can control operation of the pump 24 and heater 82 that are driven electrically. The switch 78 physically controls the "power on" or "power off" state of the sensor instrument 18. Once it is at the "power on" state, the microcomputer module 50 is in charge for power distribution to the heater 82 and pump 24, which is particularly important for a power consumption of the battery powered sensor instrument.

It will be appreciated that, in the above disclosure, appropriate interfaces that are required for connecting modules to the microcomputer are important, so that all modules can work appropriately.

As illustrated above, the metallic sensor compartment 30 can shield electromagnetic radiation, which will prevent influence to performance of the sensor instrument if it is comprised of the at least two sensors 1. Additional circuit configurations can be implemented for eliminating the electromagnetic influence. For example, referring to FIG. 8, an electronic switch 56 can be optionally added to connect to the at least two sensors 1 and the detection module 40, wherein the switch 56 is also controlled by the microcomputer module 50. Therefore, under instructions of the microcomputer module 50, the AC excitation signals with swept frequencies can be sequentially and periodically applied to each of the at least two sensors. This results in that only one of the at least two sensors will be excited at one time moment, so that the influence from the AC electromagnetic cross talk can be completely removed. This circuit configuration is practically appropriate since a speed of frequency sweeping is fast, so that the desired frequencies can be swept during a time duration of testing each of the at least two sensors.

Referring to FIG. 8, the local receiving site 96 is comprised of an antenna or antenna means 100 that connects to a transceiver 98, which is connected to digital module having a CPU. Therefore, the high frequency signal encoded with the digital data of the analyte electrical information and position, which is received by the site 96, can be decoded back to the digital data since the transmission module 68 and the site 96 have the same transmission protocol. Therefore, the digital data can be transferred to the central computer 92 of the central station 90. In a preferred embodiment for the network means 130 that is the Internet, the digital data can be transferred as a file or an e-mail attachment through file sharing or an e-mail that is the service accessible via the Internet.

Figure 12:
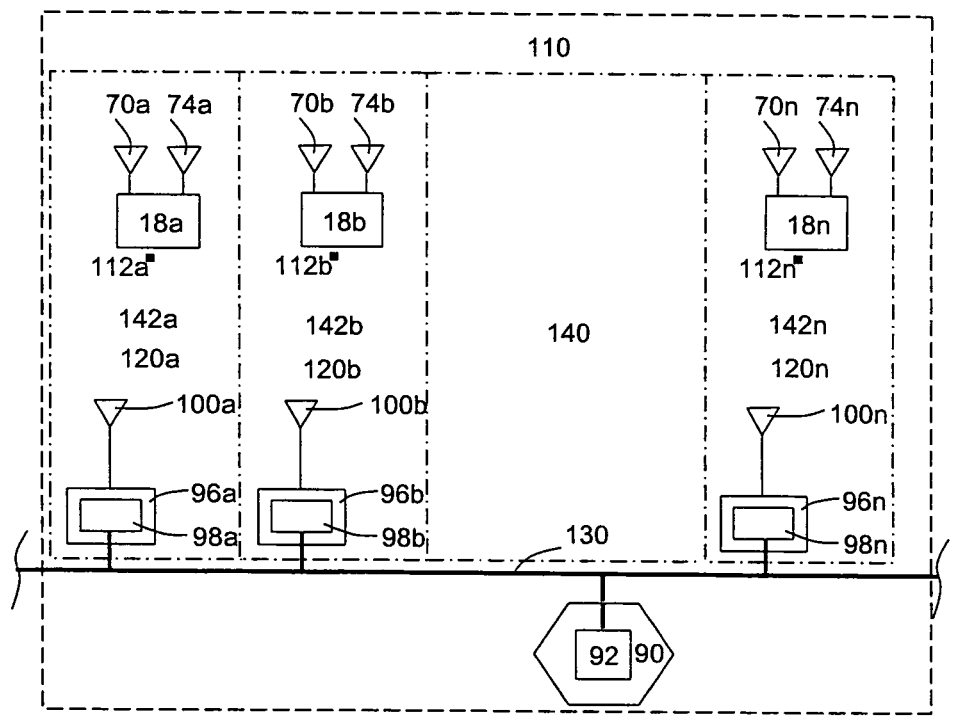
FIG. 12 shows a schematic diagram of another embodiment of the present invention sensor instrument system, comprising a central station through the network means to connect a plurality of receiving sites positioned locally, and a plurality of the sensor instruments positioned at the respective local areas of a region for wirelessly communicating with the remote central station.

In addition, referring to FIG. 12, for another embodiment of the present invention, there are a plurality of the identical local receiving sites 96a, 96b, and 96n having the respective antennas or antenna means 100a, 100b, . . . and 100n, which are positioned in a region 140 having a plurality of the respective local areas 142a, 142b, . . . and 142n, wherein the local sites are connected to the network means 130. In this embodiment, one sensor instrument 18a is comprised of a transmission antenna or antenna means 70a and a UPS antenna or antenna means 74a, which is movably positioned in the local area 142a that is covered by a local wireless communication environment 120a. The instrument 18a can wirelessly communicate to with one of the respective local receiving sites, such as the local site 96a that is positioned at the same local area 142a. In addition, the instrument 18a also can communicate with the GPS environment 110 covering the region 140 to thereby detect a geographic position 112a of the instrument 18a. Therefore, the position 112a along with the detected analyte electrical information can be wirelessly transmitted to the local receiving site 96a, and then transferred to the central station 90. Following this analogy, it results in that the sensor instrument 18a can be positioned at any local area of the region 140 to communicate with the central station 90.

Still referring to FIG. 12, in another embodiment for the system configuration, a plurality of the identical sensor instruments 18a, 18b, . . . and 18n have the respective antennas or antenna means 70a, 70b, . . . and 70n for wireless data transmission, and the respective antennas or antenna means 74a, 74b, . . . and 74n for detection of the respective GPS positions. The instruments, which are movably positioned at the respective local areas 142a, 142b, . . . and 142n of the region 140, can communicate in order with the central station 90, through the respective local wireless communication environments 120a, 120b, . . . and 120n to the respective local receiving sites 96a, 96b, . . . and 96n. As further illustrated in FIG. 12, the respective geographic positions are detected as 112a, 112b, . . . and 112n. Therefore, information of the positions 112a, 112b, . . . and 112n along with the respective analyte electrical properties can be received by the central station 90, so that an in situ mapping of analytes in the region 140 can be completed at the same time moment.

It will be appreciated that, the above illustrated wireless data communication is not limited in regions of a planet. In fact, such communication can occur among planets as long as the communication environment 120 (120a, 120b, . . . 120n) can cover a space between two planets, for example, the space between the Earth and Mars. Therefore, if the sensor instrument 18 can be placed on Mars in a robotic fashion, volatile chemicals of Mars can also be detected and identified according to two embodiments of data transmission, wherein the central station 90 that connects to the receiving cite 96 (96a, 96b, . . . 96n) is positioned on the Earth.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

The present invention has been described in considerable detail in order to comply with the patent laws by providing full public disclosure of at least one of its forms. However, such detailed description is not intended in any way to limit the broad features or principles of the present invention. Although the above invention is described in some detail by way of illustration and example for purposes of clarity of understanding, it is apparent to those of ordinary skill in the art in light of the teaching of this invention that many changes and modifications may be made thereto without departing from the scope of the appended claims.

What is claimed is:
1. A sensor instrument system, comprising:
a. a central station remote to a sensor instrument, said instrument includes a first sensor electrically connected to a detection module, a transmission module and a global positioning system (GPS) receiver module;
b. said first sensor includes first and second electrodes that are electrically separated by a first nonconductive material, wherein said first sensor is brought into contact with a portion of a sample of a fluid containing an analyte to thereby provide a detectable information for said analyte in said fluid;
c. said detection module is configured to generate a multiplicity of frequencies of alternating current (AC) signals of a group which have a same magnitude and are applied to said first sensor, and thereby measure said detectable information based on said group of said applied frequencies, wherein said detectable information comprises two AC related electrical properties at each of said applied frequencies of said AC signals for said analyte in said fluid;
d. said GPS receiver module locates a geographic position of said analyte which is detected;
e. said transmission module is in electrical communication with said detection and GPS receiver modules for transmitting data of said detectable information and said located geographic position to said central station; and
f. said central station including means for storing said data and means for analyzing said detectable information in accordance with frequencies in a selected subgroup of said applied frequencies of said AC signals to thereby identify said analyte.

2. The system as claimed in claim 1, further comprising said AC related electrical properties include impedance, resistance, reactance, phase angle, voltage and current.

3. The system as claimed in claim 1, further comprising said first sensor serves as an analytical sensor and includes said first nonconductive material that is selected from the group consisting of polymer, polymer inorganic material composite, molecular sieves, particles of silica gel, alumina, porous carbon, calcium carbonate and fluorocarbon, liquid organic salts having organoammonium or organophosphonium cations coupled with nucleophilic anions or inorganic anions, composite of one of platinum group metals having ruthenium, rhodium, palladium, osmium, iridium, and platinum composited by filler consisting of inorganic or organic materials, polymer modified porous ceramic particles including porous alumina, or polymer modified porous silica particles, polymer modified fluorocarbon particles, polymer modified porous glass beads, and polymer coated solid support particles for preparation of a packed column.

4. The system as claimed in claim 3, said sensor instrument further comprising a second sensor having third and fourth electrodes that are electrically separated by a second nonconductive material identical to said first nonconductive material, said second sensor serves as a reference sensor which is identical to said analytical sensor for compensation of background influence including polymer film aging, humidity level and variations of electrical properties of said analytical sensor caused by temperature variations, wherein said reference sensor is electrically connected to said detection module.

5. The system as claimed in claim 4, further comprising said analytical sensor and reference sensor are disposable.

6. The system as claimed in claim 4, further comprising implementing means for temperature programming to said analytical and reference sensors.

7. The system as claimed in claim 4, wherein said first, second, third, and fourth electrodes are spatial electrodes, or are positioned onto the respective ceramic substrates, or are positioned onto the respective silicon substrates.

8. The system as claimed in claim 7, further comprising surfaces of the respective solid support particles, ceramic and silicon substrates are treated with a surface treatment reagent including dimethyldichlorosilane, hexamethyldisilazane, trimethylchlorosilane, octadecyldimethylchlorosilane, or any combination thereof.

9. The system as claimed in claim 4, further comprising means for electromagnetically shielding to said analytical sensor and reference sensor.

10. The system as claimed in claim 4, further comprising a third nonconductive material is identical to said first nonconductive material and is located in front of said reference sensor, the remaining portion of said sample of said fluid containing said analyte separately flows towards said reference sensor to thereby come into contact with said third nonconductive material, so that said analyte is retained and said fluid is not retained by said third nonconductive material which results in only said fluid without having said analyte that is brought into contact with said reference sensor, said reference sensor is applied with said multiplicity of said frequencies of said AC signals of said group to thereby provide a detectable information for said fluid, wherein said detectable information comprises two AC related electrical properties at each of said applied frequencies of said AC signals for said fluid.

11. The system as claimed in claim 10, further comprising means for combining said electrical properties for said analyte in said fluid with said electrical properties for said fluid without having said analyte to obtain combined electrical properties of said analyte, and said combined electrical properties are capable of identifying said analyte in accordance with frequencies in a selected subgroup of said applied frequencies of said AC signals.

12. The system as claimed in claim 10, further comprising said analyte in said fluid flows through said analytical sensor and said fluid without having said analyte flows through said reference sensors in a laminar flow fashion.

13. The system as claimed in claim 1, further comprising said sensor instrument comprises a third sensor which is selected from the group consisting of a metal oxide thin film resistor sensor, conductive polymer sensor, polymer coated quartz crystal microbalance sensor, polymer coated surface acoustic wave sensor, metal-oxide-silicon field-effect-transistor sensor, dye coated optical fiber sensor, dye-impregnated bread array, micromachined cantilver array, polymer carbon black chemiresistor sensor, electrically conductive sensor comprising alternating regions of a conductive material and a material compositionally different than the conductive material between two conductive leads wherein said sensor provides an electrical path through the regions of conductive material and the regions of the compositionally different material, and any combination thereof.

14. The system as claimed in claim 1, further comprising a local receiving site having means for electrically communicating with said instrument, said local receiving site is electrically connected to said central station through connection of a network means comprising an Ethernet, an intranet, the internet, and the Internet linked by fiber-optical cables, metal wires, and wireless connection including electromagnetic waves.

15. The system as claimed in claim 1, further comprising said detection module including an analog to digital converter.

16. The system as claimed in claim 1, further comprising said sample is an environmental sample, which is selected from the group consisting of an environmental air sample, a headspace of an environmental liquid, and a headspace of an environmental solid.

17. The system as claimed in claim 1, further comprising said sample is a biological sample, which is selected from the group consisting of a body odor sample, a breath sample, headspaces of the respective urine sample, blood sample, stool sample, serum sample and saliva sample.

18. The system as claimed in claim 1, further comprising said sample is an anaesthetic sample.

19. The system as claimed in claim 1, further comprising said sample has an identity.

20. The system as claimed in claim 1, further comprising said central station includes means for comparing said detectable information in accordance with said frequencies in said selected subgroup for said analyte with information of the respective known analytes which is prestored in a database of said central station.

21. The system as claimed in claim 20, further comprising said central station includes means for comparing a pattern of said detectable information in accordance with said frequencies in said selected subgroup for said analyte with patterns of said information of the respective known analytes which are prestored in said database of said central station.

22. The system as claimed in claim 21, further comprising a pattern recognition algorithm of principal component analysis capable of identifying said pattern of said detectable information for said analyte.

23. The system as claimed in claim 22, further comprising additional analysis algorithms respectively capable of analyzing said detectable information for said analyte, wherein said additional analysis algorithms comprising soft independent modeling of class analogy, k nearest neighbor, hierarchical cluster analysis, canonical discriminant analysis, classical least squares, principal component regression, partial least squares regression, supervised and unsupervised learning neural network, fuzzy neural network techniques, and combination thereof.

24. The system as claimed in claim 1, further comprising said analyte is selected from the group consisting of studies of materials containing illegal substances, environment concerns, medical interests including hospital concerns, scientific and research interests including space research interests, interests of industrial sectors including food, beverages, agricultural, chemical, petroleum, plastic, construction, pharmaceutical, automobile, biochemical, and transportation, consumer interests including perfume, cosmetic, wine and flavor, and safety concerns including explosive, arson and road spill investigation.

25. The system as claimed in claim 1, further comprising said frequencies of said AC signals are selected from the group consisting of a sinusoidal wave having swept frequencies and a multiplicity of sinusoidal waves having the respective different frequencies.

26. The system as claimed in claim 1, further comprising said sensor instrument includes sample handling, heating and power modules that are respectively and electrically connected to a microcomputer module that is electrically connected to said detection, transmission and GPS receiver modules, wherein said heating module includes an exterior heater attached to an exterior surface of a sensor compartment of a sensor compartment module of said sensor instrument.

27. The system as claimed in claim 1, further comprising said sensor instrument providing selection of starting frequency, stopping frequency and said magnitude of said AC signals.

28. A sensor instrument system, comprising: a sensor instrument, said instrument comprises a dual sensor electrically connected to a detection module that is in electrical communication with a transmission module, wherein:
   a. said dual sensor including a first sensor serving as an analytical sensor and a second sensor serving as a reference sensor identical to said analytical sensor, wherein said analytical sensor comprises first and second electrodes that are electrically separated by a first nonconductive material, said reference sensor comprises third and fourth electrodes that are electrically separated by a second nonconductive material which is identical to said first nonconductive material, said analytical sensor is brought into contact with a first fluid containing an analyte, said reference sensor is brought into contact with a second fluid that is identical to said first fluid but does not contain said analyte;
   b. said detection module is configured to generate a multiplicity of frequencies of alternating current (AC) signals of a group which have a same magnitude and are applied to said analytical sensor contacted with said first fluid containing said analyte, and thereby measure a detectable information for said analytical sensor based on said group of said applied frequencies wherein said detectable information comprises two AC related electrical properties at each of said applied frequencies, said detection module is configured to generate said multiplicity of said frequencies of said alternating current (AC) signals of said group which have said same magnitude and are applied to said reference sensor contacted with said second fluid, and thereby measure a detectable information for said reference sensor based on said group of said applied frequencies wherein said detectable information comprises two AC related electrical properties at each of said applied frequencies, combined AC related electrical properties are obtained for said analyte by combining said AC related electrical properties of said analytical sensor with the respective AC related electrical properties of said reference sensor, said combined AC related electrical properties are capable of identifying said analyte according to frequencies in a selected subgroup of said applied frequencies; and
   c. said transmission module transmits data of said identified analyte.

29. The system as claimed in claim 28, further comprising said first nonconductive material is selected from the group consisting of polymer, polymer inorganic material composite, molecular sieves, particles of silica gel, alumina, porous carbon, calcium carbonate and fluorocarbon, liquid organic salts having organoammonium or organophosphonium cations coupled with nucleophilic anions or inorganic anions, composite of one of platinum group metals having ruthenium, rhodium, palladium, osmium, iridium, and platinum composited by filler consisting of inorganic or organic materials, polymer modified porous ceramic particles including porous alumina, or polymer modified porous silica particles, polymer modified fluorocarbon particles and polymer modified porous glass beads, and polymer coated solid support particles for preparation of a packed column.

30. The system as claimed in claim 28, further comprising a central station in electrical communication with said sensor instrument wherein said central station is capable of storing and displaying said data of said identified analyte.

31. The system as claimed in claim 28, further comprising said analyte is selected from the group consisting of studies of materials containing illegal substances, environment concerns, medical interests including hospital concerns, scientific and research interests including space research interests, interests of industrial sectors including food, beverages, agricultural, chemical, petroleum, plastic, construction, pharmaceutical, automobile, biochemical, and transportation, consumer interests including perfume, cosmetic, wine and flavor, and safety concerns including explosive, arson and road spill investigation.

32. A sensor instrument system, comprising: a sensor instrument, said instrument including a sensor electrically connected to a detection module that is in electrical communication with a transmission module, wherein:

a. said sensor comprises first and second electrodes that are electrically separated by an air gap, said sensor is brought into contact with a fluid containing an analyte;

b. said detection module is configured to generate a multiplicity of frequencies of alternating current (AC) signals of a group which have a same magnitude and are applied to said sensor contacted with said fluid containing said analyte, and thereby measure a detectable information of said sensor based on said group of said applied frequencies, wherein said detectable information comprises two AC related electrical properties at each of said applied frequencies, said AC related electrical properties are capable of identifying said analyte according to frequencies in a selected subgroup of said applied frequencies of said AC signals; and c. said transmission module transmits data of said identified analyte.

33. The system as claimed in claim 32, further comprising a central station in electrical communication with said sensor instrument wherein said central station is capable of storing and displaying said data of said identified analyte.

\* \* \* \* \*